US011793982B2

(12) United States Patent
Lee et al.

(10) Patent No.: US 11,793,982 B2
(45) Date of Patent: Oct. 24, 2023

(54) DRUG DELIVERY DEVICES AND METHODS OF FABRICATION AND USE THEREFOR

(71) Applicants: Purdue Research Foundation, West Lafayette, IN (US); Industry-University Cooperation Foundation Hanyang University, Seoul (KR)

(72) Inventors: Chi Hwan Lee, West Lafayette, IN (US); Yoon Yeo, West Lafayette, IN (US); Dong Rip Kim, Seoul (KR)

(73) Assignees: Purdue Research Foundation, West Lafayette, IN (US); Industry-University Cooperation Foundation Hanyang University, Seoul (KR)

( * ) Notice: Subject to any disclaimer, the term of this patent is extended or adjusted under 35 U.S.C. 154(b) by 209 days.

(21) Appl. No.: 17/344,362

(22) Filed: Jun. 10, 2021

(65) Prior Publication Data
US 2021/0386986 A1    Dec. 16, 2021

Related U.S. Application Data

(60) Provisional application No. 63/037,127, filed on Jun. 10, 2020.

(51) Int. Cl.
*A61M 37/00* (2006.01)

(52) U.S. Cl.
CPC .  *A61M 37/0015* (2013.01); *A61M 2037/0023* (2013.01); *A61M 2037/0053* (2013.01); *A61M 2205/0244* (2013.01)

(58) Field of Classification Search
CPC ...... A61M 37/0015; A61M 2037/0023; A61M 2037/0053; A61M 2205/0244; A61M 2037/0061
See application file for complete search history.

(56) References Cited

U.S. PATENT DOCUMENTS

2014/0194379 A1\*   7/2014  Rolandi  ...............  A61L 31/042
604/173

OTHER PUBLICATIONS

Aykul et al. "Determination of Half-Maximal Inhibitory Concentration Using Biosensor-Based Protein Interaction Analysis", 2016, Anal. Biochem.; 508: 97-103. (Year: 2016).\*
Chiappini, C. et al., "Biodegradable Silicon Nanoneedles Delivering Nucleic Acids Intracellularly Induce Localized In Vivo Neovascularization," Nat. Mater. 2015, 14, 532-539.
Fang, Y. et al., "Texturing Silicon Nanowires for Highly Localized Optical Modulation of Cellular Dynamics," Nano Lett. 2018, 18, 4487-4492.

(Continued)

*Primary Examiner* — Amber R Stiles
(74) *Attorney, Agent, or Firm* — Hartman Global IP Law; Gary M. Hartman; Domenica N. S. Hartman

(57) ABSTRACT

Drug delivery devices that have a flexible film, an array of nanoscopic, porous needles attached to a surface of the flexible film, and a therapeutic drug cargo loaded onto the needles. The drug delivery device may be applied to living tissue such that the surface of the flexible film contacts the living tissue and some or all of the needles are inserted into the tissue. The flexible film may then be dissolved while leaving the needles inserted in the tissue. The needles degrade in the living tissue over time causing release of the therapeutic drug cargo loaded onto the needles.

16 Claims, 21 Drawing Sheets

(56) References Cited

OTHER PUBLICATIONS

Gopal, S. et al., "Porous Silicon Nanoneedles Modulate Endocytosis to Deliver Biological Payloads," Adv. Mater. 2019, 31, 1-8.
Kim, H. et al., "Flexible Elastomer Patch with Vertical Silicon Nanoneedles for Intracellular and Intratissue Nanoinjection of Biomolecules," Sci. Adv. 2018, 4, 1-8.
Li, W. et al., "Rapidly Separable Microneedle Patch for the Sustained Release of a Contraceptive," Nat. Biomed. Eng. 2019, 3, 220-230.

* cited by examiner

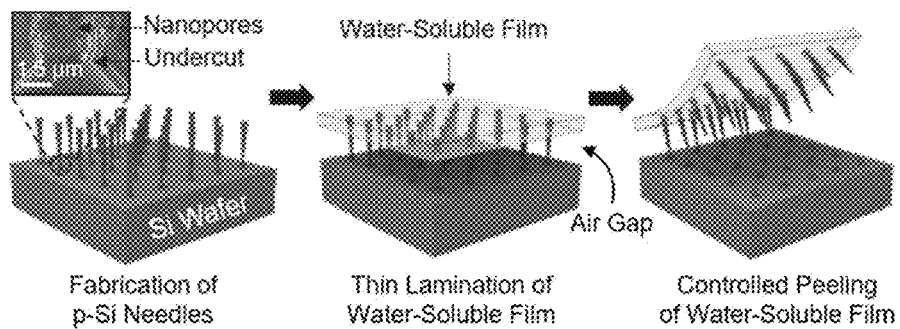
FIG. 1A
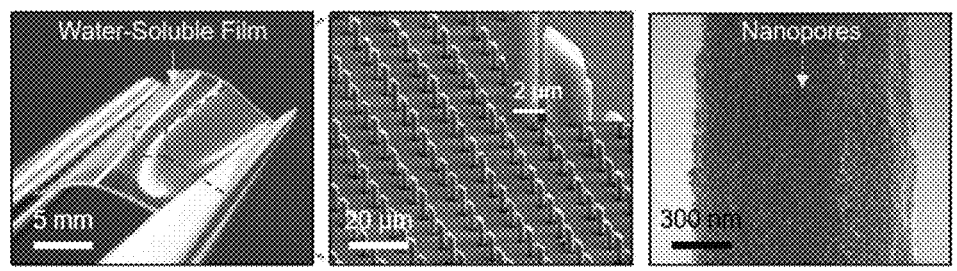
FIG. 1B    FIG. 1C
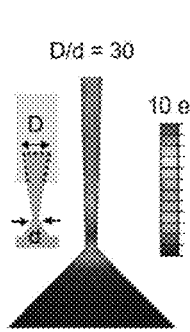 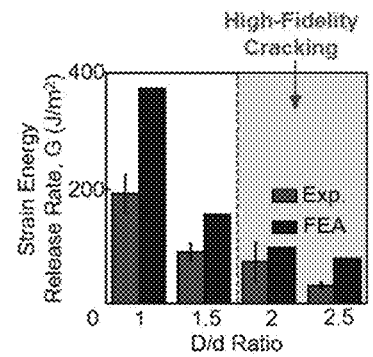 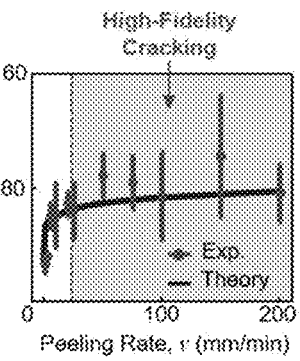
FIG. 1D    FIG. 1E    FIG. 1F

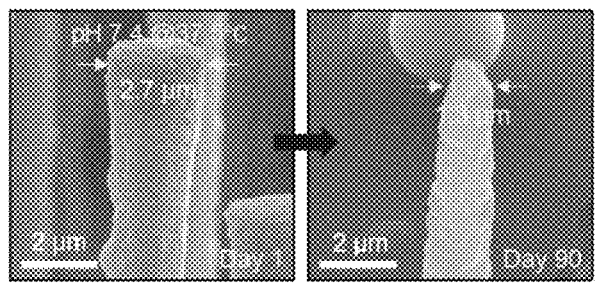 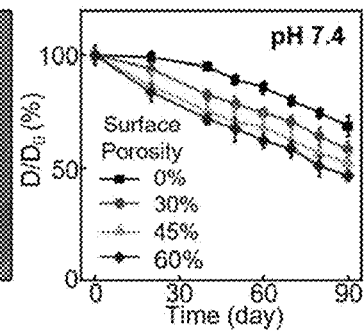
FIG. 2A  FIG. 2B
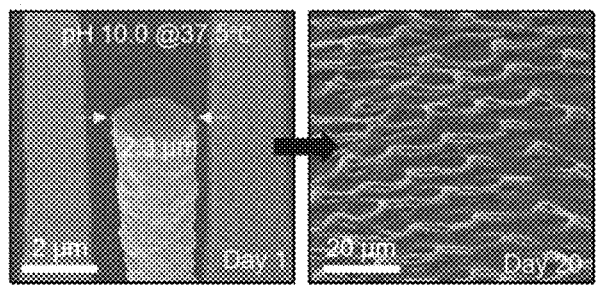 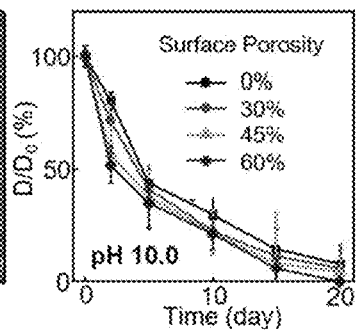
FIG. 2C  FIG. 2D
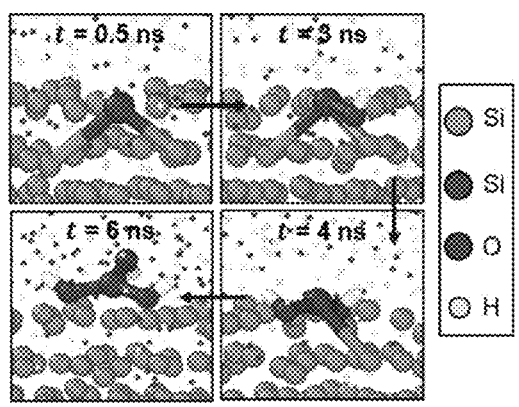 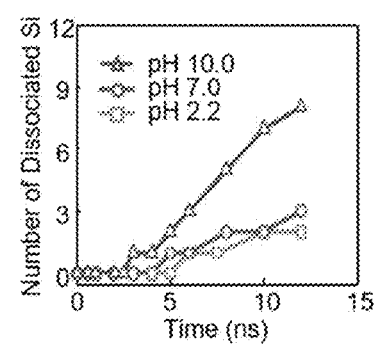
FIG. 2E  FIG. 2F

DRUG DELIVERY DEVICES AND METHODS OF FABRICATION AND USE THEREFOR

CROSS REFERENCE TO RELATED APPLICATIONS

This application claims the benefit of U.S. Provisional Application No. 63/037,127, filed Jun. 10, 2020, the contents of which are incorporated herein by reference.

STATEMENT REGARDING FEDERALLY SPONSORED RESEARCH

This invention was made with government support under Contract Nos. FA2386-16-1-4105 and FA2386-18-1-4071 awarded by the Air Force Office of Scientific Research (AFOSR) and under Grant No. R01 CA199663 awarded by the U.S. National Institutes of Health (NIH). The government has certain rights in the invention.

BACKGROUND OF THE INVENTION

The present invention generally relates to topical drug delivery devices. The invention particularly relates to drug delivery devices having nanoscopic needles on a substrate with therapeutic drugs loaded onto the needles, as well as to methods of fabricating and using such delivery devices.

Melanoma, the most serious form of skin cancer, is typically caused by ultraviolet radiation from natural sunshine or tanning beds and developed at the stratum corneum of epidermis (about 15-25 μm from the skin surface). Given the aggressive and recurrent nature of melanoma cells, repeated treatments are often necessary, thereby increasing the risk of toxicity and side effects. An effective treatment involves using the topical administration of chemotherapeutics into tumor tissues using polymeric microneedles fabricated on a substrate, which offers a relatively less-invasive and painless route than traditional treatments. The microneedles are typically characterized by a level of surface porosity that determines at least in part the drug loading capacity of the microneedles, in other words, the amount of a drug that can be loaded onto a microneedle, for example, through conjugation (e.g., covalent bonding (linking) or non-covalent bonding) of the drug to the surfaces of p-Si needles. A drug loaded (conjugated) onto the microneedles is sometimes referred to as the "drug cargo" of the needles.

Recently, further miniaturized nanoscale needles made of porous-silicon (p-Si) has emerged as an attractive candidate for intratissue injection that can offer a favorable safety profile and controlled biodegradability. Compared to conventional polymeric microneedles, the nanoscale p-Si needles benefit from their amenability to existing nanofabrication processing, and therefore provide several advantages including: precise control of the size, geometry, tapering, and tip morphology of the p-Si needles at the nanoscale level; rational tuning of porosity on the surfaces of the p-Si needles to influence the drug loading capacity of the p-Si needles; uniform delivery of the drug cargo of the p-Si needles owing to the high density of the needles per projected surface area; pre-programmable dissolution rate of the p-Si needles through surface oxidations (encapsulation); and long-lasting release of the drug cargo thereto by gradual degradation of the p-Si needles in tissue fluids over time. These attributes promote controlled, sustained, and minimally-invasive topical delivery of therapeutics.

Challenges still remain, particularly in regard to fabrication of vertically-ordered arrays of nanoscale p-Si needles on a rigid substrate, for example, a silicon (Si) wafer, to accommodate the conditions required for conventional nanofabrication processing, such as thermal annealing, corrosive chemical etching, and photolithographic patterning. The use of a rigid Si wafer results in a mechanical mismatch when interfaced with the soft, curvilinear, and dynamic surfaces of living tissues. This discordance leads to debasing of the interfacial contact quality, which is particularly problematic in their application to the small, curvilinear, and exceptionally-sensitive cornea where melanoma is occasionally formed (ocular melanomas).

Attempts have been made to alleviate these challenges to some extent by building nanoscale p-Si needles on a thin, flexible substrate (film) made of a silicone elastomer such as polydimethylsiloxane (PDMS) for their use in intracellular drug delivery. Despite the benefits of this approach, in some cases a PDMS film may cause irritation or discomfort to the wearer especially under vigorous deformations of tissues by body movements.

In view of the above, it can be appreciated that there are certain problems, shortcomings or disadvantages associated with topical administration of chemotherapeutics into tumor tissues using nanoscale polymeric needles, and that it would be desirable if systems and methods were available that were capable of at least partly overcoming or avoiding the issues relating to the fabrication of nanoscale polymeric needles on a flexible substrate.

BRIEF DESCRIPTION OF THE INVENTION

The present invention provides drug delivery devices that include nanoscale p-Si needles and methods of use thereof suitable for topical delivery of therapeutic drug cargos to living tissue.

According to one aspect of the invention, a drug delivery device is provided that includes a flexible film, an array of nanoscopic, porous needles attached to a surface of the flexible film, and therapeutic drug cargos loaded on individual needles of the array of nanoscopic, porous needles.

According to another aspect of the invention, a method is provided that includes providing a drug delivery device that includes an array of nanoscopic, porous needles attached to a surface of a flexible film, applying the drug delivery device to living tissue such that the surface of the flexible film contacts the living tissue and some or all of the needles are inserted into the tissue, and dissolving the flexible film while leaving the inserted needles in the tissue. The needles degrade in the living tissue over time causing release of therapeutic drug cargos that were loaded onto the needles.

Technical effects of drug delivery devices and methods as described above preferably include the ability to topically treat living tissue with minimal physical discomfort.

Other aspects and advantages of this invention will be appreciated from the following detailed description.

BRIEF DESCRIPTION OF THE DRAWINGS

FIGS. 1A through 1F represent a nonlimiting architecture and details relating to a fabrication process for a drug delivery device in accordance with certain aspects of the present invention. FIG. 1A schematically represents construction of the device including nanoscale p-Si needles on a water-soluble film. The inset image highlights a bottom undercut and nanopores at the bottom and on the surface of the p-Si needles, respectively. FIG. 1B includes optical images of p-Si needles integrated with a polyvinyl alcohol (PVA) film. The inset image highlights the sharpened angular tip of the p-Si needles. FIG. 1C includes an SEM image of nanopores formed on the surface of p-Si needles. FIG. 1D contains representative finite element analysis (FEA) results showing the distribution of principal strains along a p-Si needle during constant peeling. FIG. 1E contains experimental and FEA results for the effect of D/d ratio on strain energy release rate (G). FIG. 1F contains experimental and theoretical results for the effect of peeling rate (v) on the strain energy release rate (G).

FIGS. 2A through 2F represent degradation of p-Si needles in biofluids. FIG. 2A includes SEM images of p-Si needles at one day (left image) and 90 days (right image) after immersing in 50 ml of phosphate-buffered saline (PBS) (pH 7.4) at 37.5° C. FIG. 2B contains measurement results of $D/D_0$ ratio (%) obtained from p-Si needles with varied surface porosities of 0%, 30%, 45%, and 60%. FIG. 2C includes SEM images of p-Si needles at one day (left image) and twenty days (right image) after immersing in 50 ml of PBS (pH 10.0) at 37.5° C. FIG. 2D contains measurement results of $D/D_0$ ratio (%) obtained from p-Si needles with varied surface porosities. FIG. 2E includes snapshot images of molecular dynamics (MD) simulation at different time frames. FIG. 2F contains results of the number of dissociated Si atoms in solutions at acidic (pH 2.2) and basic (pH 10.0) conditions formed by the addition of $H^+$ and $OH^-$ groups, respectively, compared to a neutral condition (pH 7.0).

FIG. 3A includes real-time bioluminescence images on the epidermis (on top of the skin) and subcutaneous muscle (under the skin) of mice at five hours following the implementation of p-Si needles built on a medical-grade PVA (left column), industrial-grade PVA (middle column), and control PMA treatments (right column). FIG. 3B contains results of MTT (3-[4,5-dimethylthiazol-2-yl]-2,5 diphenyl tetrazolium bromide) assay in the cytotoxicity tests of human dermal fibroblast (HDF) cells incubated with a medical-grade PVA with and without p-Si needles, as well as an industrial-grade PVA. Error bars represent the standard deviation (SD) of three replicates. ****$p<0.0001$ compared to the medical-grade PVA with p-Si needles using one-way analysis of variance (ANOVA). FIG. 3C contains a confocal microscopy image of the p-Si needles loaded with a chemotherapy drug doxorubicin (DOX). FIG. 3D contains a confocal microscopy image of p-Si needles embedded inside a 2.8% (w/v) agarose gel (color index by penetration length). FIG. 3E represents cumulative release of DOX obtained from p-Si needles with varied surface porosities of 0%, 30%, 45% and 60% after twenty days of immersion in PBS (pH 7.4) at 37.5° C. *$p<0.05$ compared to 0% surface porosity using ANOVA. FIG. 3F contains release profiles obtained from p-Si needles with covalently-linked DOX, compared to median lethal dose of DOX in mice ($LD_{50}$, horizontal dotted line). FIG. 3G shows release profiles obtained from p-Si needles with a surface porosity of about 45% using amide, urea, and control physical bonds of DOX. $p<0.01$ and **$p<0.0001$ compared to the control physical bond using ANOVA. FIG. 3H represents cumulative release (%) of the covalently-linked (amide and urea bonds) DOX, compared to the control physically trapped DOX.

FIG. 4A includes optical images of the p-Si needles with fluorescent dyes (DyLight™ 800) on a PVA film, applied to the epidermis (left image), subcutaneous muscle (middle image), and cornea (right image) of mice. FIG. 4B includes images obtained with an IVIS® Spectrum in vivo imaging system (commercially available from PerkinElmer) of the mice interfaced with the p-Si needles for two days following the implementations.

FIG. 5A includes schematic illustrations of experimental protocols for in vivo studies in a murine melanoma model. FIG. 5B contains a representative optical image of the shaved skin of a mouse post-nanoinjection of DOX. FIG. 5C represents measurement results of the tumor size for twelve days post-inoculation (n=5 per group). *$p<0.05$ compared to the control syringe injection (DOX) using ANOVA. FIG. 5D represents a radial shape graph of the tumor size at day ten (n=5 per group). FIG. 5E represents measurement results of the body weight for twelve days post-inoculation (n=5 per group). FIG. 5F includes representative optical images highlighting the treated sites after ten days post-injection. The dotted circle denotes skin lesions.

DETAILED DESCRIPTION OF THE INVENTION

Figures 3A, 3B:
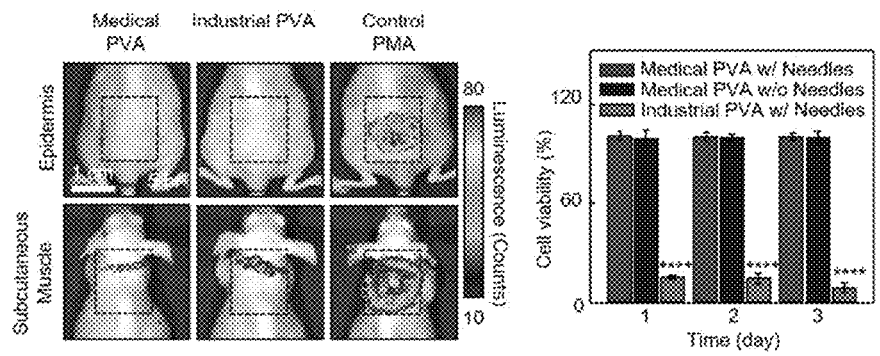
FIGS. 3A through 3H represent biocompatibility and controlled drug release of the drug delivery device of FIG. 1.

Disclosed herein are drug delivery devices and methods for their fabrication and use. The delivery devices have an array of bioresorbable, miniaturized porous-silicon (p-Si) needles that are attached to and project from a surface of a flexible substrate, generally referred to herein as a flexible film (or simply film) that is also preferably water soluble. The devices are capable of being loaded with therapeutic drug cargos that are fluidically coupled to the needles. The devices may be used for therapeutic treatments such as but not limited to topical administration of chemotherapeutics into tumor tissues. For example, the devices may be applied to living tissue such that a surface of the flexible film comprising the needles contacts and preferable conforms to the living tissue and at least some of, preferably most or all of, the needles penetrate and are inserted into the tissue. Subsequently, the flexible film may be dissolved such that the inserted needles remain embedded in the tissue.

In the case of a water-soluble film, the flexible film may be dissolved by application of a water-based solution to the film such as but not limited to a saline solution or interstitial fluid. In some cases, the film may be dissolved in one minute or less after application of the device to the living tissue to avoid any discomfort or physical restrictions. Once the film is completely dissolved, the remaining p-Si needles embedded in the tissue preferably become unobtrusive (nearly unnoticeable) to a wearer without affecting their natural motions due to their miniaturized size. Over time, the needles degrade in the living tissue causing release of the drug cargos that were loaded onto the needles, for example, via gradual hydrolysis due to the action of fluids in the living tissue.

As such, the film may be used as a temporary substrate during the insertion of p-Si needles into living tissues, and can be subsequently dissolved by the application of an appropriate solution, for example, a water-based solution. This allows for the needles to be delivered to target tissue where they preferably degrade into biocompatible byproducts, leading to sustained, long-lasting release of pre-loaded drug cargos over time (e.g., days) at a predetermined controlled rate.

As used herein, the term "p-Si needle" refers to a nanoscale or nanoscopic needle that is generally conical or tubular in shape and has geometric features that include minimum tip diameters of less than 1 µm, base diameters of less than 10 µm, and lengths of at least 1 µm. p-Si needles disclosed herein preferably have minimum tip diameters of about 50 to 900 nm, base diameters of about 0.9 to 5 µm, and lengths of about 1 to 100 µm, and more preferably minimum tip diameters of about 150 nm, base diameters of about 2 to 4 µm, and lengths of about 10 to 70 µm.

The size and thickness of the film may be adjusted depending on the size and shape of the living tissue to which it is intended to be applied in order to provide predetermined flexibility and dissolution times. One aspect is that the films are sufficiently flexible to conform to contours of the human anatomy to be treated, in which case these films are preferably relatively thin, for example, less than one millimeter in thickness, and in some cases less than 500 micrometers. However, the films must also be sufficiently thick to provide mechanical strength for handling, which in some cases may require a thickness of at least 200 micrometers.

The porosity of the p-Si needles relates to the loading capacity and release rate of their drug cargos. The porosity of the p-Si needles may range from about 0 to about 80 percent, for example, from about 0 to 60 percent. In certain embodiments, the p-Si needles preferably have an average porosity of about 15 to 60 percent, more preferably between about 25 to 50 percent, for example, about 45 percent. In certain embodiments, the drug delivery devices may have a drug loading capacity of 10 µg or more per 1×1 cm$^2$ area of the surface of the film to which the p-Si needles are attached, as a nonlimiting example, 15 µg to about 50 µg, per 1×1 cm$^2$.

The drug delivery devices may have a drug release profile that includes a rapid release of their drug cargos within 24 hours post-inoculation until they gradually reach a sustained, predetermined dose that is released and maintained for a period of time. In such embodiments, 24 hours or less after the inoculation, the drug delivery devices preferably provide a sustained release dose sufficient to provide a therapeutic effect for the application (e.g., at or above a minimum inhibitory concentration for the drug of interest), and more preferably provide a sustained release dose above a half maximal inhibitory concentration ($IC_{50}$) value for the application. Such sustained releases at the predetermined doses (e.g., after the initial rapid release) preferably last for a period of time of at least 24 hours, for example, up to about 3 days. Such sustained release doses and time periods may be controlled based on the specific application.

FIG. 1A schematically represents a nonlimiting method for integration of bioresorbable, miniaturized p-Si needles with a thin, flexible, and water-soluble medical film, such as polyvinyl alcohol (PVA; medical-grade; mechanical modulus (E)=3.4 GPa; molecular weight of about 31,000). In this nonlimiting example, an array of vertically-ordered p-Si needles may be initially fabricated on a polished monocrystalline Si wafer through sequential steps of photolithographic patterning, dry and wet etchings, and metal-assisted chemical etching (MACE) (FIG. 1A, left). This step also forms uniform undercuts and nanopores at the bottom and on the surface of p-Si needles, respectively (inset image).

The fabrication process may include immersing a bulk Si wafer (p-type; e.g. about 525 µm-thick and about 0 to about 100 Ω·cm) in a solution of buffered oxide etch for one minute to eliminate any native oxide layer thereon. Following a standard photolithographic patterning, a deep reactive-ion etching (DRIE) may be carried out under a radiofrequency (RF) plasma power of, for example, 450 W and a platen power of, for example, 11 W using sulfur hexafluoride ($SF_6$) gas with the flow rate of, for example, 85 sccm to create vertically-ordered Si micropillars at a prescribed aspect ratio. The deposition of a $(C_xF_y)_n$ polymer may be followed to form a partial passivation layer using octafluorocyclobutane ($C_4F_8$) gas with the flow rate of, for example, 130 sccm under the RF plasma power of, for example, 800 W. Additional isotropic dry etching under the plasma power of, for example, 450 W and platen power of, for example, 30 W by $SF_6$ gas with the flow rate of, for example, 85 sccm may be conducted to create undercuts at the bottom of the Si micropillars. The entire specimen may then be treated with an oxygen ($O_2$) plasma (e.g., 20 sccm, 150 W, 50 mtorr, 15 min), followed by cleaning with standard piranha solution (75% of sulfuric acid ($H_2SO_4$) and 25% of hydrogen peroxides ($H_2O_2$)) to eliminate the remaining passivation layer on the surface of the Si micropillars.

Figure 6:
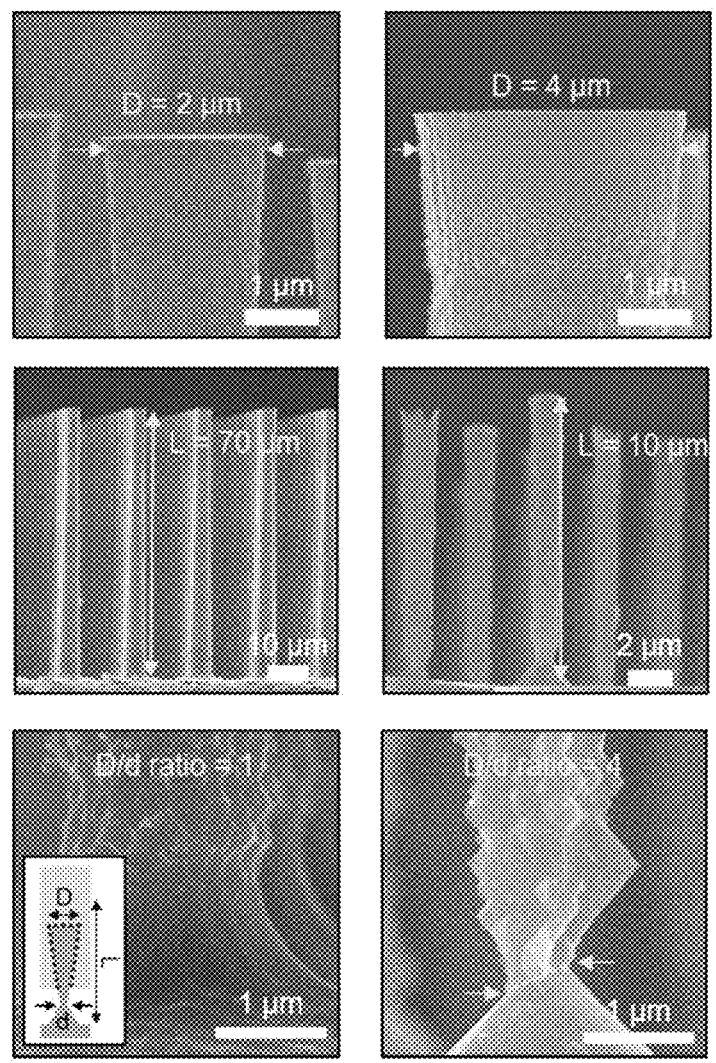
FIG. 6 includes scanning electron microscope (SEM) images of p-Si needles fabricated on a donor Si wafer with varied geometries. The inset schematic image denotes a base diameter (D) and undercut diameter (d) of the p-Si needles.

Finally, the entire specimen may be immersed in a solution of potassium hydroxide (KOH; 15 wt %) at 25° C. to reduce the overall size of the Si micropillars, preferably down to the nanoscale. The overall size of the miniaturized Si pillars may be determined by controlling the molarity of etching solution, temperature, and etching time. The next step involves the MACE by immersing the specimen in a mixed solution of 20 mM silver nitrate ($AgNO_3$) and 49% hydrofluoric acid (HF) to form nanopores on the surface. During the MACE, the overall surface porosity was controlled by adjusting the etching time. The specimen was then immersed in a solution of silver etchant (TFS, KI-I2 complex liquid) for one minute to remove the remaining silver residues on the surface. FIG. 6 shows representative scanning electron microscopy (SEM) images of p-Si needles fabricated according to this process, exhibiting a minimum tip diameter (d) of 150 nm, a base diameter (D) of 2-4 μm, and a length (L) of 10-70 μm.

Figure 7A:
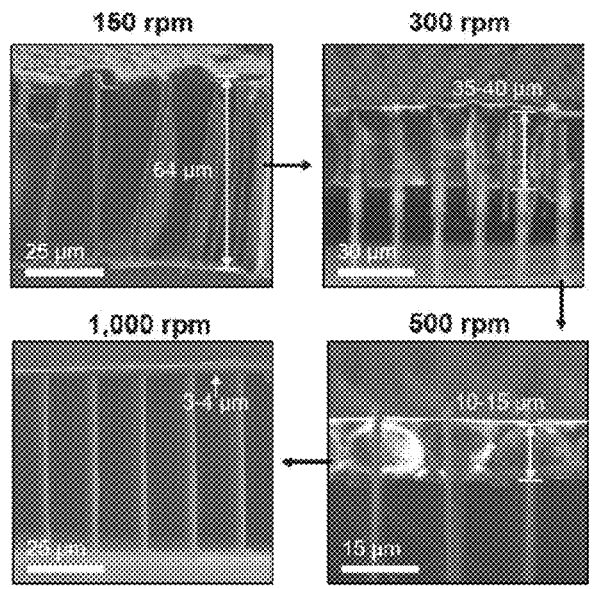
FIG. 7A includes SEM images of a PVA film coated on p-Si needles at varied spin-casting speeds of 150, 300, 500, and 1000 rpm.
Figure 7B:
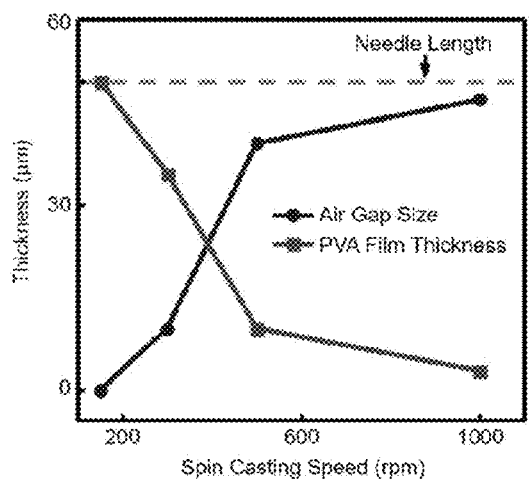
FIG. 7B includes a plot of measured thicknesses of PVA film and air gap size as a function of spin casting speed ranging from 150 rpm to 1000 rpm.

After fabrication on the Si wafer is complete, the entire structure may be spin-cast with a pre-cured solution of 10 wt % PVA (200-300 μm-thick) or 5.5 wt % PLGA (lactide: glycolide (50:50)), allowing an air gap to form at the interface due to surface tension (FIG. 1A, middle). The length of the p-Si needles and the thickness of the film are determined by this air gap that may be adjusted by controlling the spin-casting speed within the range from, for example, 300 rpm to 500 rpm, leading to the consequent air gap size of about 20 μm and about 50 μm, respectively (FIGS. 7A and 7B).

The spin-casting of the film may be repeated until its total thickness reaches at least about 200-300 μm to provide sufficient mechanical strength for handling. Subsequently, a thermal annealing may be performed to complete the solidification of the film using a convection oven maintained at, for example, 70° C. for 30 minutes. Finally, the fully cured film may be peeled from the Si wafer at constant peeling rate of, for example, 50 mm/min using an automated peeling apparatus (FIG. 1A, right). During this peeling process, mechanical stress can be concentrated predominantly at the bottom undercuts of the p-Si needles to generate cracks allowing for their physical liberation from the Si wafer.

Various therapeutic drug cargos may be loaded onto the p-Si needles. Covalent and non-covalent conjugation of drug cargos are believed to be capable of providing reliable drug loading onto the surfaces of the p-Si needles and sustained releasing behavior from the surfaces of the p-Si needles. For example, the chemotherapy drug doxorubicin (DOX) may be loaded by covalent bonding onto the needles via 3-triethoxysilylpropyl succinic anhydride (TESPSA) as a cross-linker. This exemplary process may begin by washing the as-fabricated p-Si needles on a Si wafer with distilled (DI) water, followed by thorough drying with nitrogen ($N_2$) gas. The cleaned p-Si needles may be immersed in a solution of 3-triethoxysilylpropyl succinic anhydride (TESPSA) for two hours to functionalize the surface with amide. Alternatively, the p-Si needles may be immersed in a solution of 3-triethoxysilylpropyl isocyanate (ICPTS) for two hours to functionalize the surface with urea. The p-Si needles may then be rinsed with ethanol and then baked at 120° C. for one hour, followed by immersing in a solution of DOX (e.g., 0.5 mg/ml) for 24 hours at room temperature.

Nonlimiting embodiments of the invention will now be described in reference to experimental investigations leading up to the invention. Specifically, comprehensive experimental and computational studies were performed to provide an insight into the structural design and construction of p-Si needles on a water-soluble film over centimeter-scale areas and analyze their fundamental attributes. Demonstrations of p-Si needles for the topical delivery of chemotherapy in a murine melanoma model illustrated the practical utility of this concept.

Figure 8:
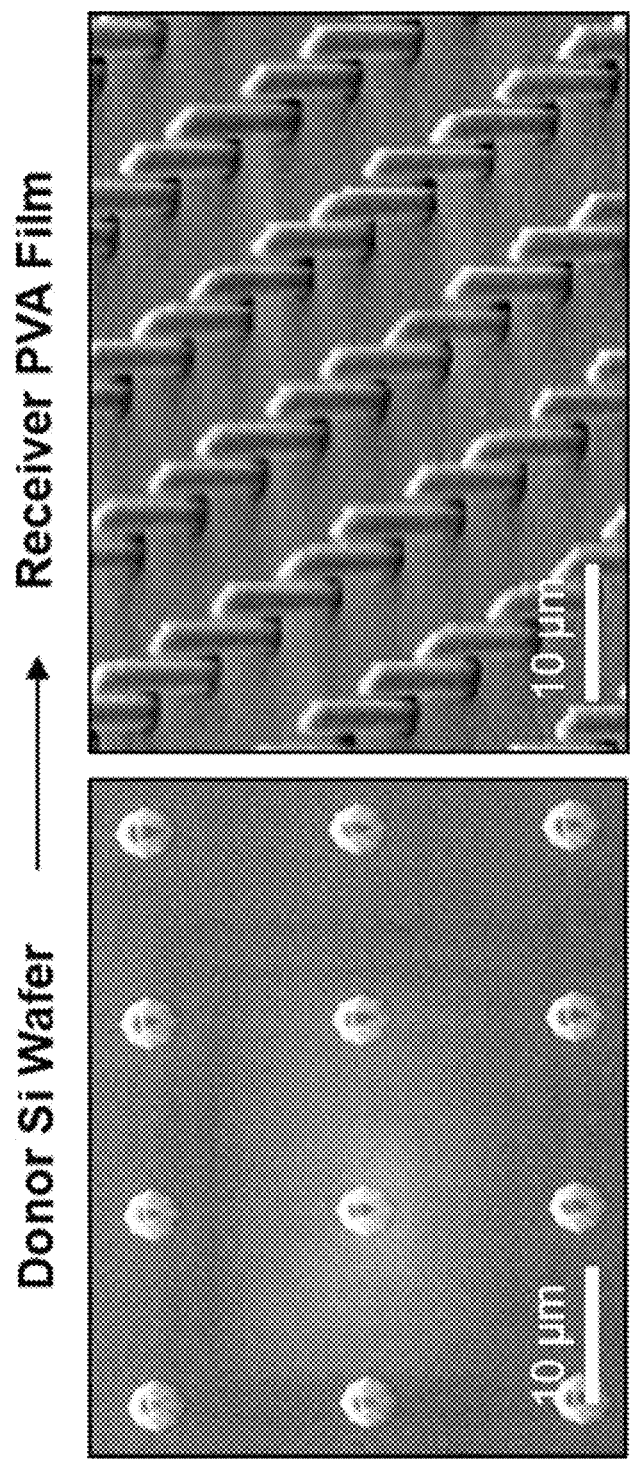
FIG. 8 includes SEM images of a donor Si wafer (left image) and a receiver PVA film (right image).
Figure 9:
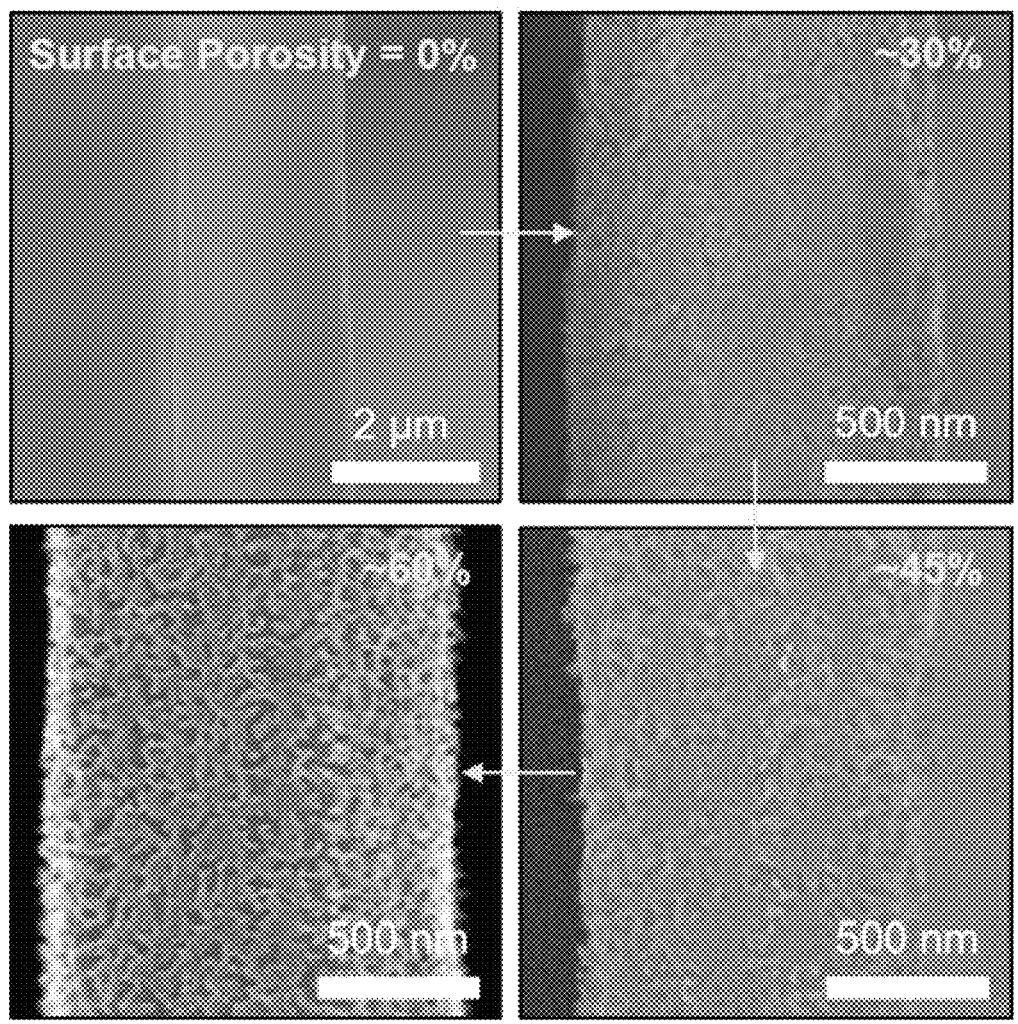
FIG. 9 includes SEM images of p-Si needles with varied surface porosities of 0%, 30%, 45%, and 60%.
Figure 10:
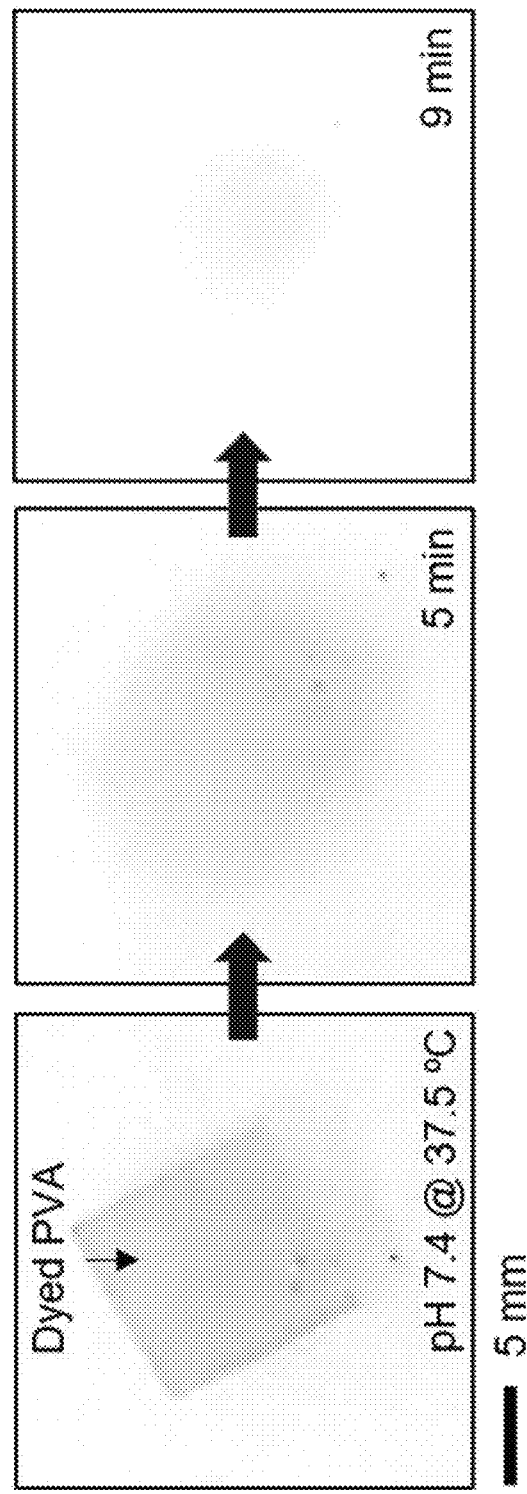
FIG. 10 includes time-dependent optical images of a PVA film immersed in a solution of PBS (pH 7.4) at 37.5° C.

FIG. 1B shows representative optical (left) and enlarged microscope images (right) of p-Si needles that were physically transferred to a thin layer (200-300 μm-thick) of a PVA film according to the above-describe process. The intrinsically thin and flexible property of the film can facilitate intimate contact to the soft, irregular surface of tissues, while the sharpened angular tip of the p-Si needles promotes penetration. The overall height, vertical arrangement, and tip morphology of the transferred p-Si needles were consistent across the entire specimen area (3×3 $cm^2$). FIG. 8 shows the fractured planes on both the donor Si wafer and the receiver PVA film, suggesting that the cracking occurred uniformly at the bottom undercut of the p-Si needles. FIG. 1C shows nanopores formed on the surface of the p-Si needles in which the porosity (in turn, drug loading capacity) can be adjusted during the MACE process. The SEM images in FIG. 9 provide representative examples of the p-Si needles configured into different surface porosities (0%, about 30%, about 45%, and about 60%) that were controlled by the MACE time of 0, 30, 60, and 90 seconds, respectively. FIG. 10 presents a series of optical images at various stages during the dissolution of the PVA film (colored with food dye for visualization) when immersed in 50 ml of phosphate-buffered saline (PBS; pH 7.4) at 37.5° C. The complete dissolution of the PVA film occurred typically within 10 to 15 minutes in this condition. Alternatively, it could be swabbed away using a saline-moistened cotton swab in less than one minute.

Figures 11A, 11B:
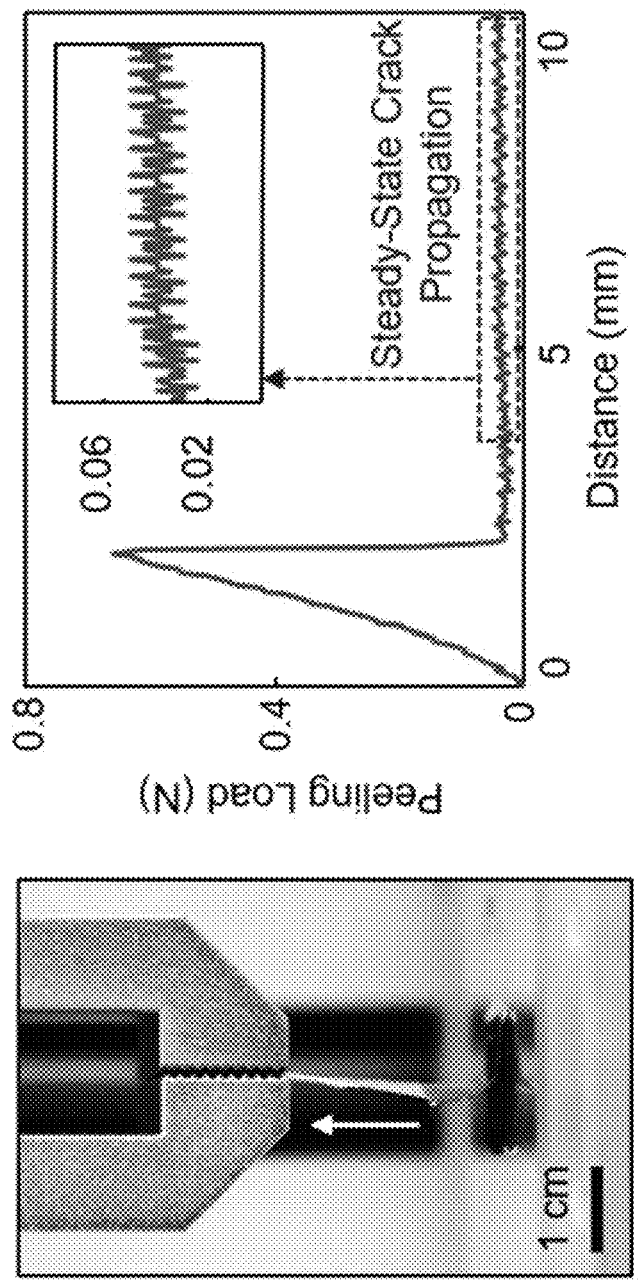
FIG. 11A is an optical image of an experimental setup for the automated peeling of p-Si needles from a donor Si wafer.
FIG. 11B represents measurement results of the peeling load obtained from a unit specimen (1×1 $cm^2$).
Figure 12:
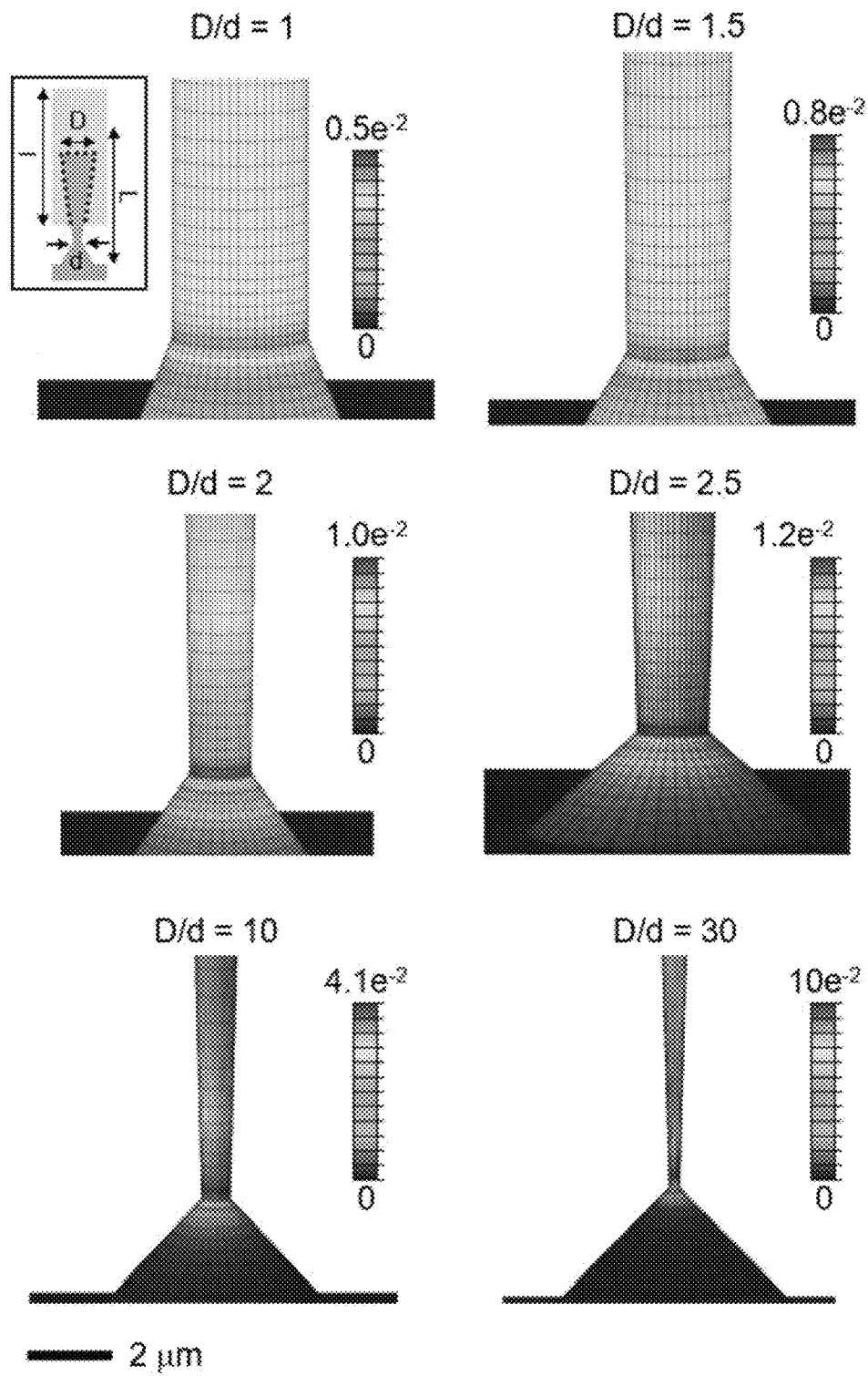
FIG. 12 includes FEA results displaying the distribution of principal strains along a p-Si nanoneedle with varied D/d ratios under constant mechanical peeling.
Figure 13:
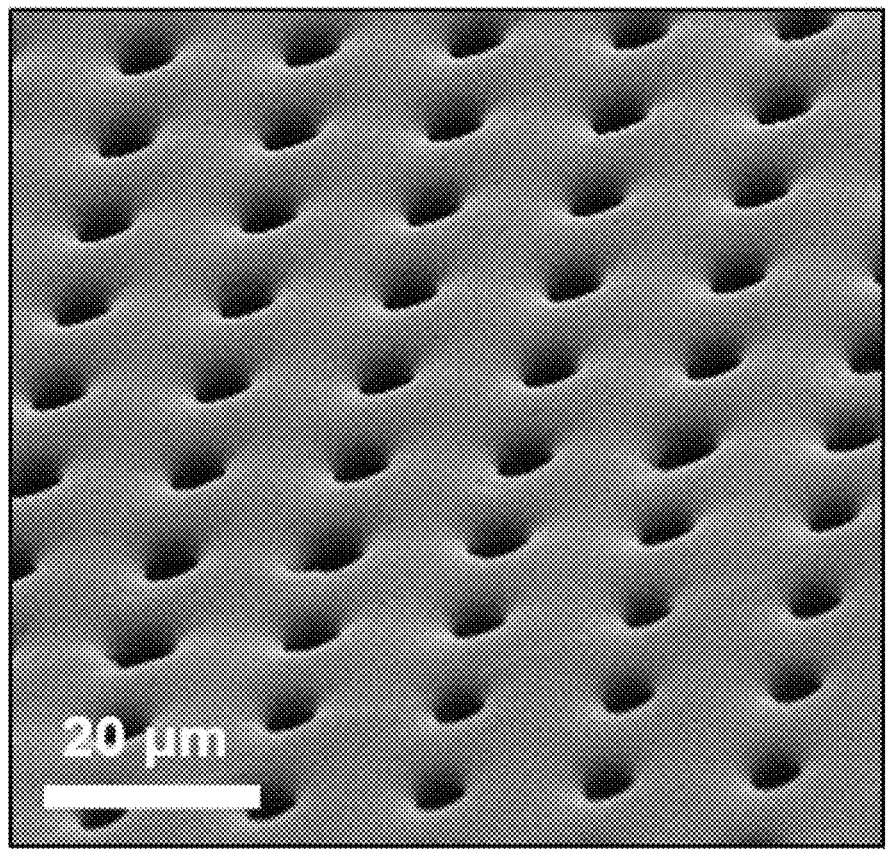
FIG. 13 is a representative SEM image displaying compressed marks remaining on a surface of a PVA film peeled out of optimal conditions.

FIG. 11 shows an experimental setup and corresponding experimental results for peeling load-peeling distance curve for a specimen (3×3 $cm^2$, d=1 μm, D=4 μm, and L=50 μm) under constant peeling of a PVA film at 50 mm/min. The results indicate that the peeling load increased rapidly to a maximum that initiated cracking, and then reached a plateau for steady-state crack propagation. FIG. 1D shows finite element analysis (FEA) results, revealing that the principal strain (ε) remained localized near the bottom undercut of p-Si needles during the constant peeling. The tendency for the localization of c was more evident as the D/d ratio was increased, wherein the peak principal strain ($ε_{peak}$) was larger than the fracture limit (about 1%) of the p-Si needles when D/d>1.5 (FIG. 12). The experimental and FEA results of strain energy release rate (G) for the cracking are summarized in FIG. 1E. The shaded area denotes where the cracking typically occurred with high-fidelity. FIG. IF experimentally and theoretically reveals the dependence of G on peeling rate (v) of the PVA film. The results showed a clear power-law relationship of them (i.e., the G increased rapidly at low v and then gradually reached steady-state) due to the viscoelastic property of the PVA film. For instance, a rapid peeling (v>20 mm/min) of the PVA film provided sufficiently large adhesive strength to peel the p-Si needles away from the Si wafer. On the other hand, a slow peeling (v<20 mm/min) of the PVA film was unable to hold the p-Si needles, resulting in compressed marks left on the surface (FIG. 13). For the theoretical analysis, the energy release rate was obtained by assuming that the PVA film was monolithically bonded to the p-Si needles without embedding inside, causing the discrepancy with the experimental results especially at high peeling rates (v>100 mm/min).

Figure 14:
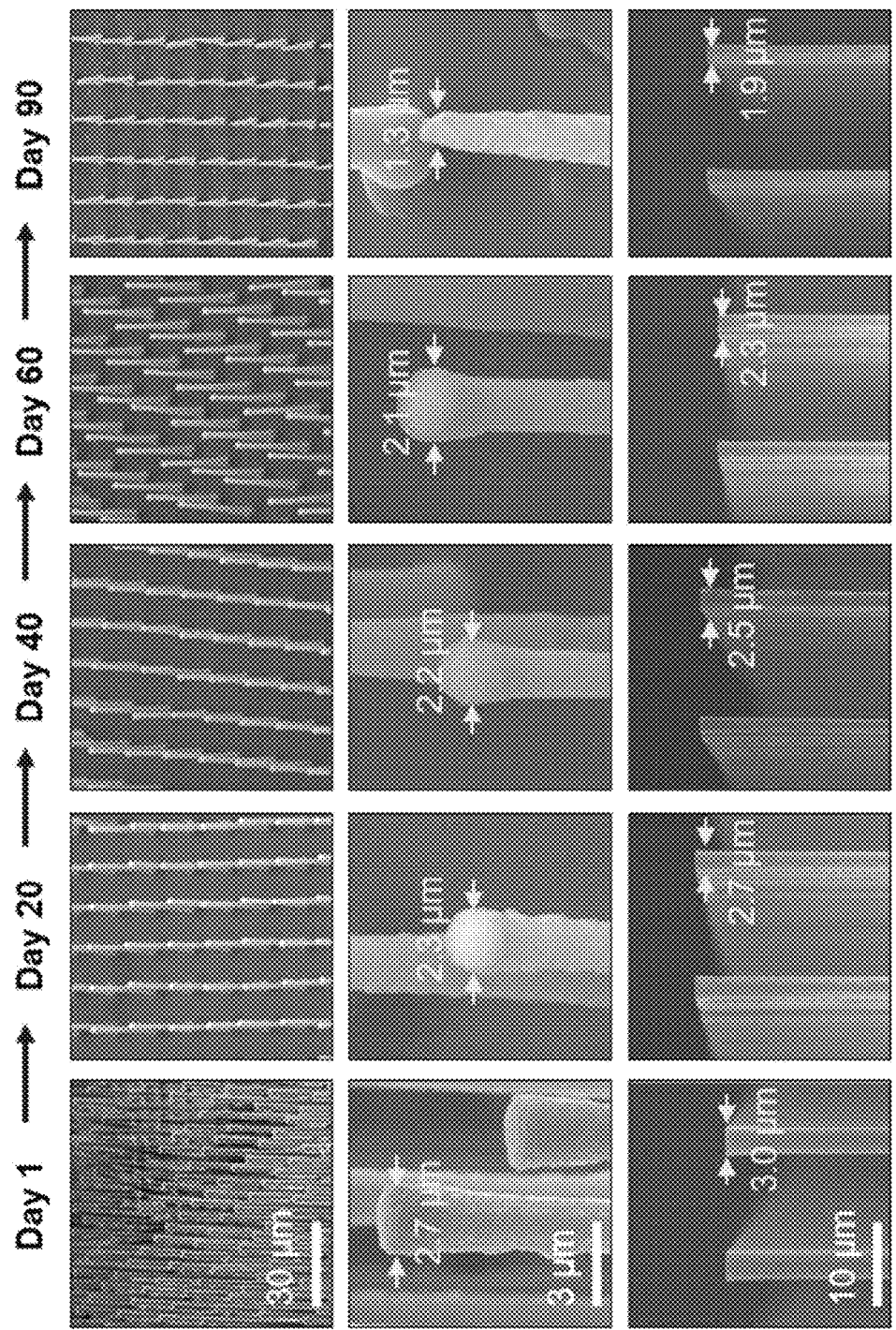
FIG. 14 includes SEM images of p-Si needles immersed in 50 ml of PBS (pH 7.4) at 37.5° C. for 90 days.

FIG. 2A shows gradual dissolution of a unit array (1×1 $cm^2$) of p-Si needles with a fixed initial base diameter ($D_0$) of 3 μm when immersed in 50 ml of PBS (pH 7.4) at 37.5° C. for ninety days, while refreshing the solution every ten days to maintain the pH value. The magnified SEM images of the p-Si needles at predetermined time intervals are shown in FIG. 14. The dissolution of the p-Si needles occurred via hydrolysis of Si to silicic acid and hydrogen (i.e., $Si+4H_2O \leftrightarrow Si(OH)_4+2H_2$), which involves nucleophilic attack at the surface to weaken the interior bonds of Si atoms. The dissolution kinetics rely on the pH, temperature, and ionic strength of the solution as well as the pre-defined surface porosity of Si. FIG. 2B shows measurement results of the gradual diameter reduction ($D/D_0$) of the p-Si needles with varied surface porosities, indicating that the dissolution rate was increased from about 10 nm/day to about 20 nm/day as the surface porosity was increased from 0% to 60%. FIGS. 2C and 2D compare the dissolution of the p-Si needles in higher pH environment (PBS; pH 10.0) at 37.5° C. The results indicate that the dissolution rate was substantially accelerated at higher pH, while the rate was non-linearly decreased over time due to enhanced dependence on the concentration of the byproducts, such as $Si(OH)_4$, in the solution. In fact, the biosafety of the monocrystalline Si nanomaterials and their dissolution products has been shown in many biomedical applications, without showing measurable cytotoxic effects.

FIG. 2E shows a series of snapshot images obtained from molecular dynamics (MD) simulation at different time frames, revealing the dissociation process of a Si atom in water ($H_2O$) due to the effect of nucleophile attack by $OH^-$ groups (enlarged). At the beginning (t=0.5 ns), no bonding occurred between the Si atom and OH— groups. At t=3 ns, an $OH^-$ group started attacking the Si atom to create a bond. At t=4 ns, a second $OH^-$ group attacked the Si atom and formed another bond to break an interior Si—Si bond. At t=6 ns, a third $OH^-$ group attacked the Si atom and finally triggered its complete dissociation. The dissociation occurred when the maximum distance of a Si atom from its nearest neighbors remained longer than 3.0 Å. FIG. 2F shows the variation of number of dissociated Si atoms in solutions at acidic (pH 2.2) and basic (pH 10.0) conditions formed by addition of $H^+$ and $OH^-$ groups, respectively, compared to a neutral condition (pH 7.0). The results show that the number was increased over the simulation time from 0 ns to 12 ns, while the dissolution was accelerated at higher pH due to the increased concentration of $OH^-$ groups. It is also anticipated that the enhanced surface porosity would also affect the reaction (dissolution) rate due to the increased contact area between the Si and liquid solution. These findings are consistent with the above-described experimental observations.

To evaluate in vivo tissue compatibility, a set of real-time bioluminescence images were captured at five hours post-injection of p-Si needles (1×1 cm², d=150 nm, D=1 μm, and L=50 μm) to the epidermis (on top of the skin; top row) and subcutaneous muscle (under the skin; bottom row) on the backside of mice (FIG. 3A). To compare the biocompatibility grade, the experiments were conducted using p-Si needles built on a medical-grade PVA film (left column), an industrial-grade PVA film (middle column), and a positive control treatment (right column) of phorbol 12-myristate 13-acetate (PMA; 1 mM, 20 μl) that promotes intense local inflammation. Both the epidermis and the subcutaneous muscle showed no evidence of inflammation following the administration of luminol (5-amino-2,3-dihydro-1,4-phthalazinedione) that detects acute inflammation at the implemented sites, whereas acute inflammation appeared in the control mice.

Figure 15A:
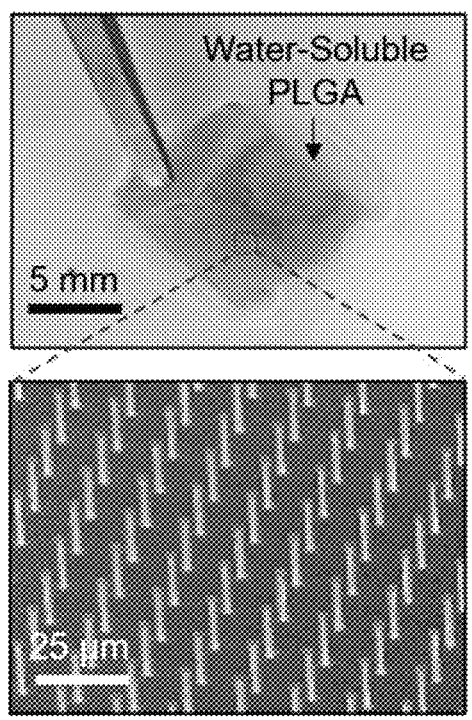
FIG. 15A includes optical (top panel) and SEM (bottom panel) images of p-Si needles built on a water-soluble poly(lactic-co-glycolic acid) (PLGA) film.
Figure 15B:
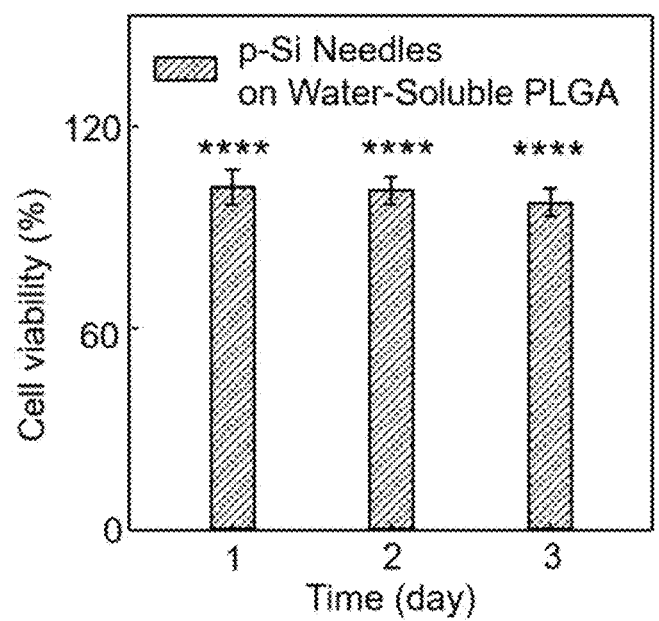
FIG. 15B represents corresponding results of MTT assay for the cytotoxicity test of HDF cells. Error bars represent the standard deviation of the three replicates. ****$p<0.0001$ compared to the industrial-grade PVA with p-Si needles using ANOVA.

Here, the industrial-grade PVA was dissolved within one minute after the insertion of the p-Si needles into the tissues by applying saline immediately, thereby causing no inflammation. FIG. 3B shows in vitro cell viability of human dermal fibroblast (HDF) cells seeded in a 24-well plate that contains the p-Si needles (1×1 cm², d=150 nm, D=2 μm, and L=20 μm) and medical-grade PVA film, as measured using a colorimetric MTT assay kit (3-(4,5-Dimethylthiazol-2-yl)-2,5-diphenyltetrazolium bromide). For these tests, the length of the p-Si needles (20 μm-long) was tailored for the HDF cells of which the average diameter is about 20-30 μm. The cell viability remained over 99.3% during the entire period (three days) of the assay without substantial difference compared to that of the control bare medical-grade PVA film without the p-Si needles. Whereas, acute toxicity appeared in the industrial-grade PVA film due to the residual ethanol and butanol. Similar results were observed in other control specimens formed by replacing the PVA film with a sheet of water-soluble poly(lactic-co-glycolic acid) (PLGA; 50/50 lactide:glycolide; molecular weight=30,000 to 60,000; E=2 GPa), providing the cell viability of greater than 97.4% (FIG. 15).

Figures 3C, 3D, 3E:
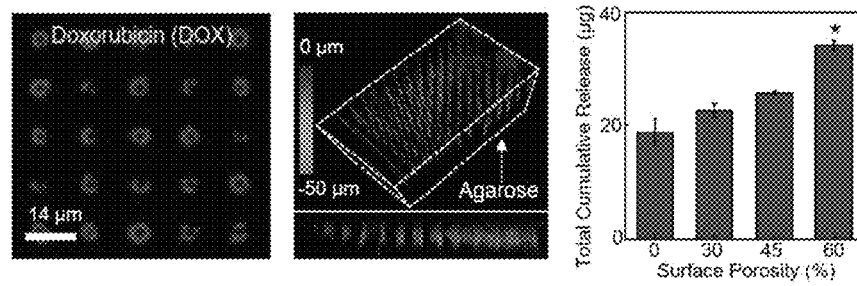
Figure 16:
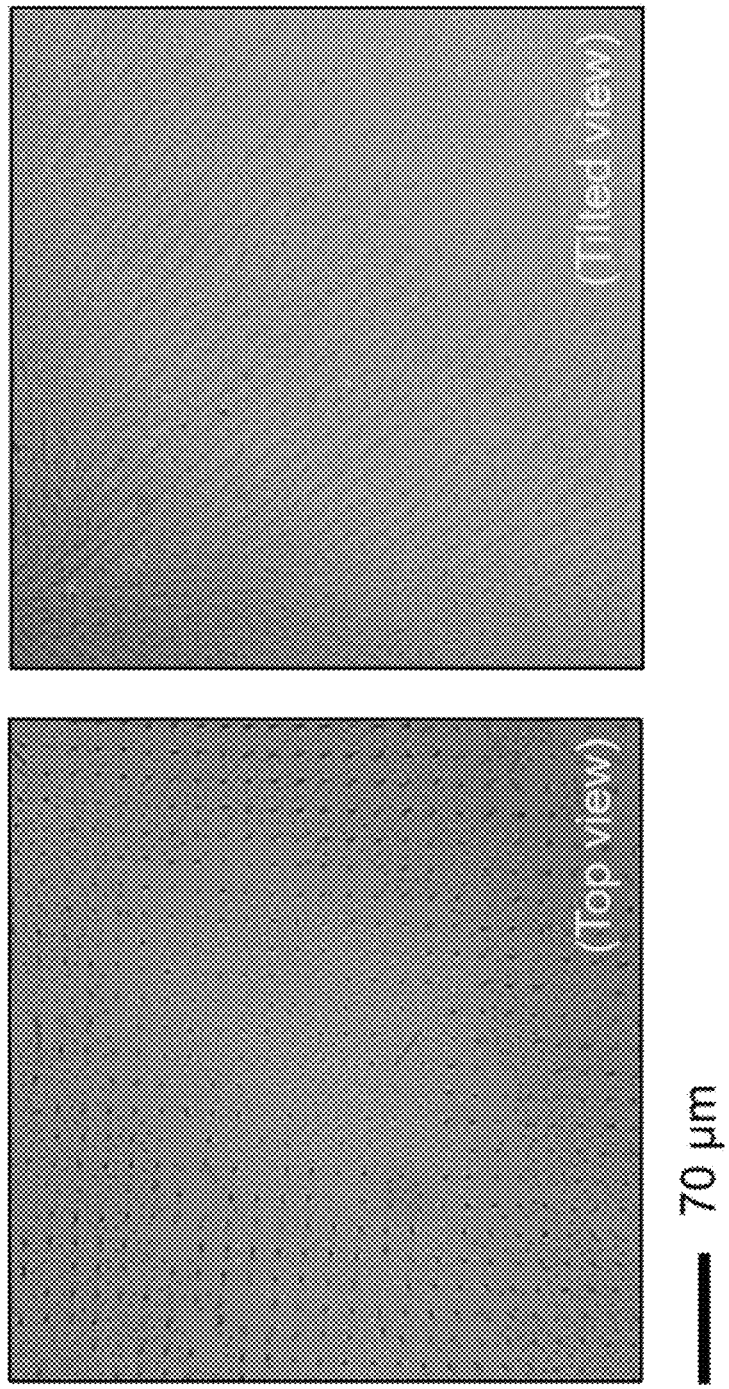
FIG. 16 includes top-view (left image) and tilted-view (right image) microscope images of p-Si needles penetrated into a 2.8% (w/v) agarose gel.

As noted above, covalent and non-covalent conjugation of drug cargos to the surface of p-Si needles can provide for reliable drug loading and sustained releasing behavior. FIG. 3C shows representative fluorescence microscopy images (top view) of p-Si needles where the surface was covalently linked with a chemotherapy drug doxorubicin (DOX) using 3-Triethoxysilylpropyl succinic anhydride (TESPSA) as a cross-linker. A confocal lens (40×) was focused at the bottom of the p-Si needles, resulting in ring-shaped fluorescence of the DOX. The peak fluorescence intensity of the DOX was observed on the surface of the p-Si needles due to high surface area of the nanopores. FIG. 3D shows a three-dimensional (3D) confocal image (tilted view) of the p-Si needles upon insertion into a soft agarose gel (2.8% w/v) that provides a comparable mechanical modulus (E=about 100 kPa) to the human tissues (E=about 80 to 150 kPa). The experiments were performed by gently pressing the PVA film with the p-Si needles (1×1 cm², d=150 nm, D=1 μm, and L=50 μm) into the agarose gel, followed by the application of saline to completely dissolve the PVA film. The side view of the image (bottom row) highlights that the p-Si needles were embedded inside the agarose gel through the full length of 50 μm. Larger-field views of the specimen are shown in FIG. 16.

Figures 3F, 3G, 3H:
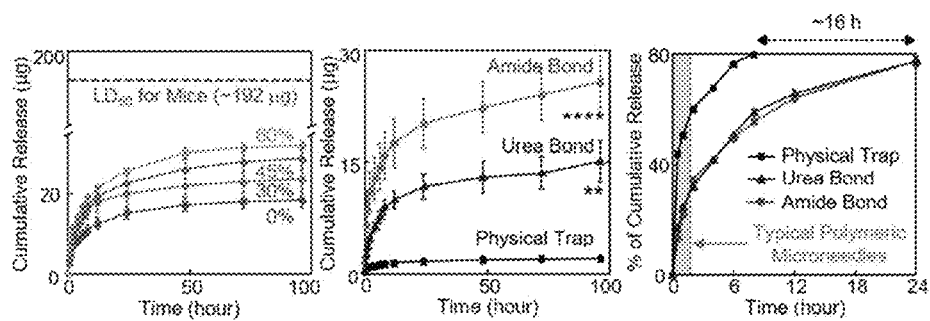

FIG. 3E shows the total cumulative amount of DOX released from p-Si needles with varied surface porosities of 0% to 60% in PBS (pH 7.4) at 37.5° C. The corresponding release profiles as a function of time (up to 100 h) are shown in FIG. 3F, exhibiting that rapid release of DOX occurred within 24 hours and then gradually reached a plateau at the predefined doses. The range of the released doses (18 to 35 μg) were comparable to those used in studies reported in the literature that used polymeric microneedles. Importantly, the released doses remained higher than the half maximal inhibitory concentration ($IC_{50}$) value (about 0.3 μg/ml) for B16F10 murine melanoma cells and substantially lower than the lethal dose ($LD_{50}$) value (about 192 μg; horizontal dash line) for mice. FIG. 3G shows the cumulative release of covalently-linked DOX using different cross-linkers of amide and urea in PBS (pH 7.4), as compared to that of physically-trapped DOX.

Figure 17:
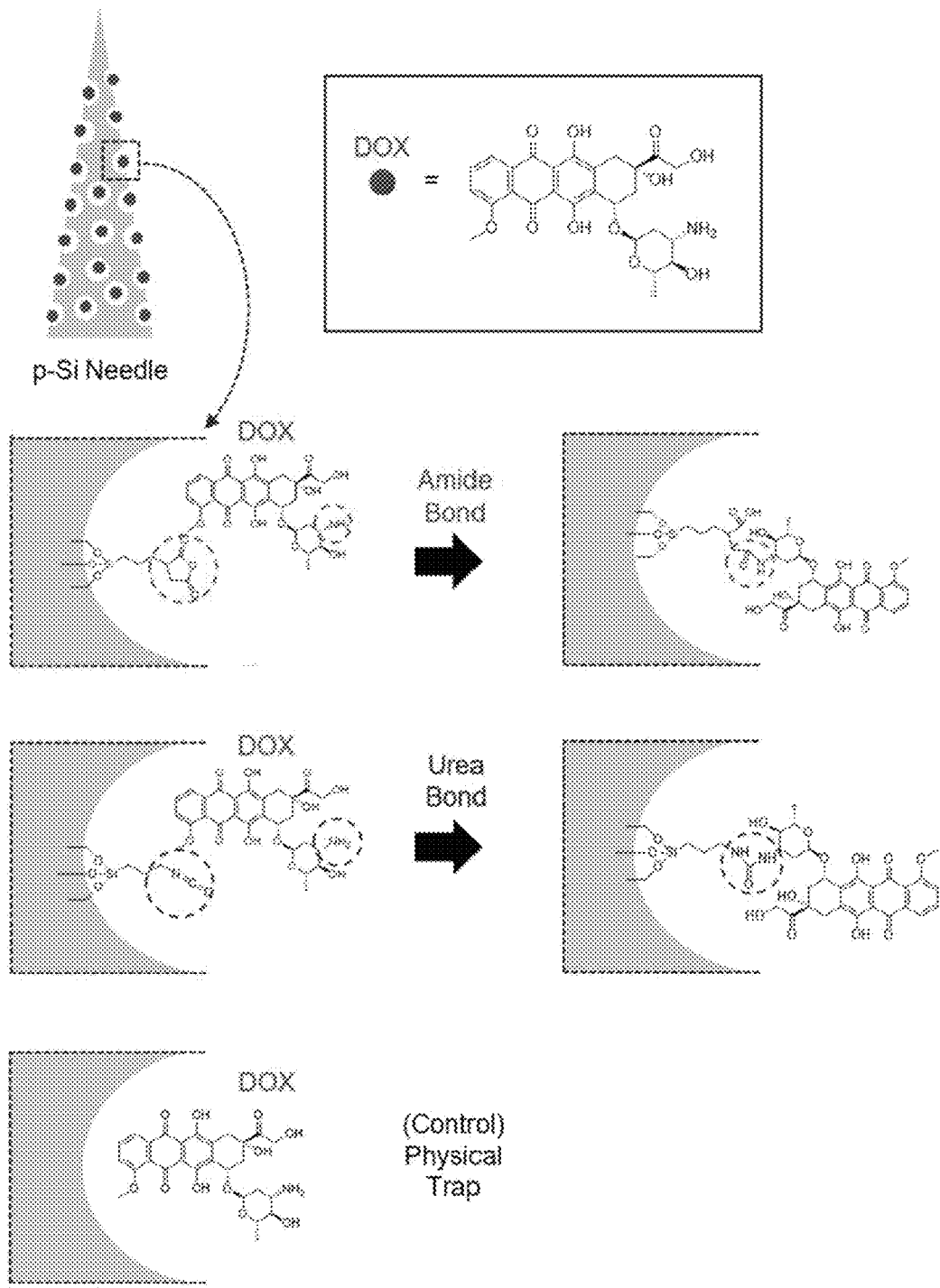
FIG. 17 includes schematic diagrams of amide, urea, and physical bonds of DOX to surfaces of p-Si needles.

For these tests, the surface porosity of the p-Si needles was fixed at about 45%. Amide and urea bonds are well-known to provide strong covalent linkages of the amine group (—NH2) of DOX to the succinic anhydride of 3-(triethoxysilyl) propylsuccinic anhydride (TESPSA) and the isocyanate (—N═C═O) of 3-isocyanatepropyl triethoxysilane (ICPTS), respectively. The control physical bond relied on relatively weak Van der Walls forces, resulting in relatively rapid and burst release of drug molecules. Schematic diagrams of these bonding mechanisms are shown in FIG. 17. The highest drug loading capacity attained occurred in the amide bond (about 25 μg) followed by the urea bond (about 15 μg), both of which were substantially higher than that of the physical trapping (about 2 μg). These observations support that the covalently-linked DOX provides strong binding affinity for the surface of the p-Si needles to form a highly stable complex at physiological pH.

The strong covalent bonding is beneficial for the sustained release of DOX by allowing the release to occur predominantly by the gradual dissolution of the p-Si needles. FIG. 3H presents the corresponding release profiles (%) as a function of time (up to 24 hours), highlighting the longer-lasting release of the covalently-linked DOX than counterparts. For instance, more than 80% of the covalently-linked DOX was released over about 24 hours, which was substantially longer than control specimens with the physically-bonded DOX (about 8 hours) and conventional polymeric microneedles (typically, 15 minutes to 2 hours; shaded area), respectively.

To illuminate the utility of p-Si needles in the envisioned scenarios of transepidermal, transmuscular, and transocular injections, a unit array of p-Si needles (1×1 cm$^2$, d=150 nm, D=1 μm, and L=50 μm) with covalently-linked (amide) fluorescent dyes was introduced to the epidermis, subcutaneous muscle, and cornea of athymic nude mice in vivo.

Figure 4A:
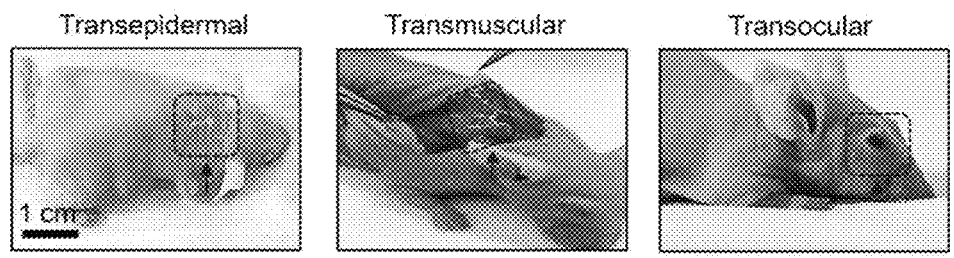
FIGS. 4A and 4B show unobtrusive topical delivery of p-Si needles.
Figure 4B:
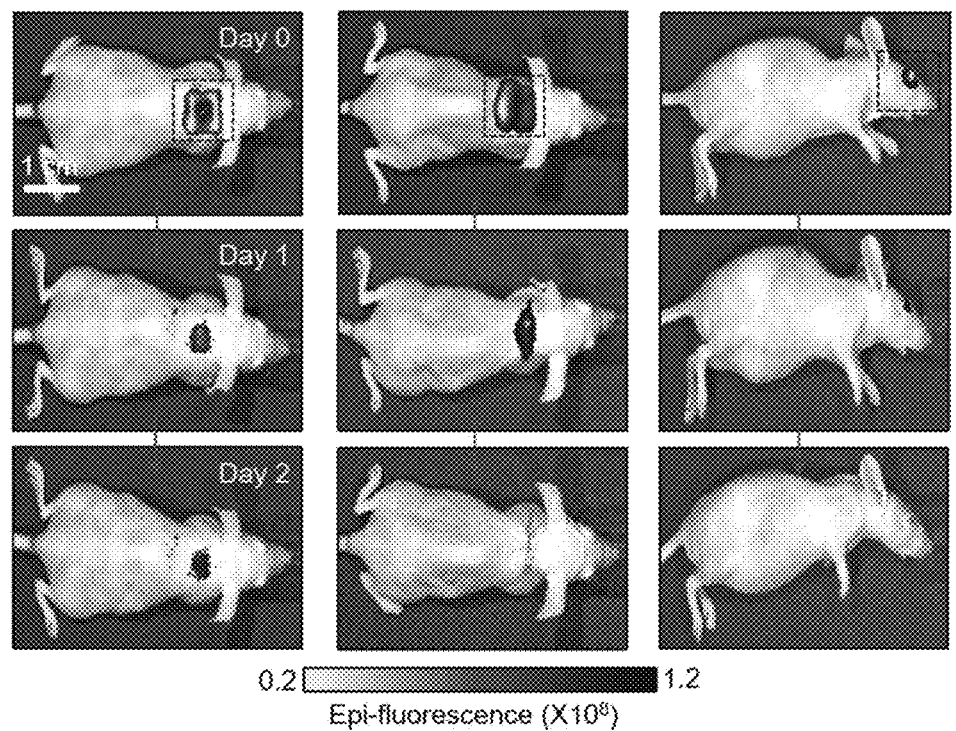
Figure 18:
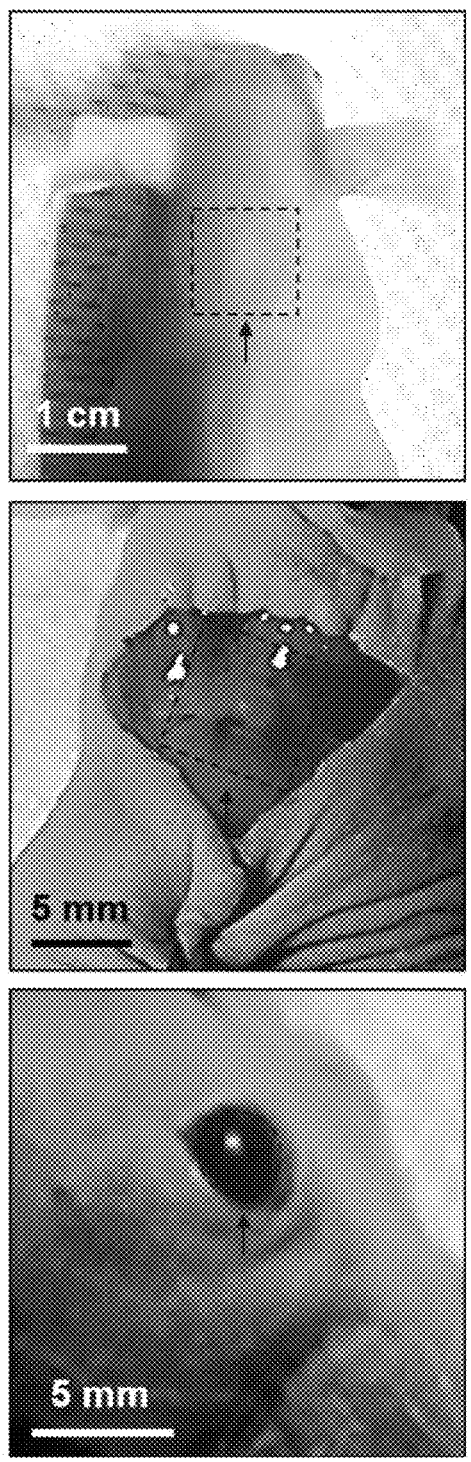
FIG. 18 includes enlarged optical images of the epidermis, subcutaneous muscle, and cornea of mice receiving p-Si needles.
Figure 19:
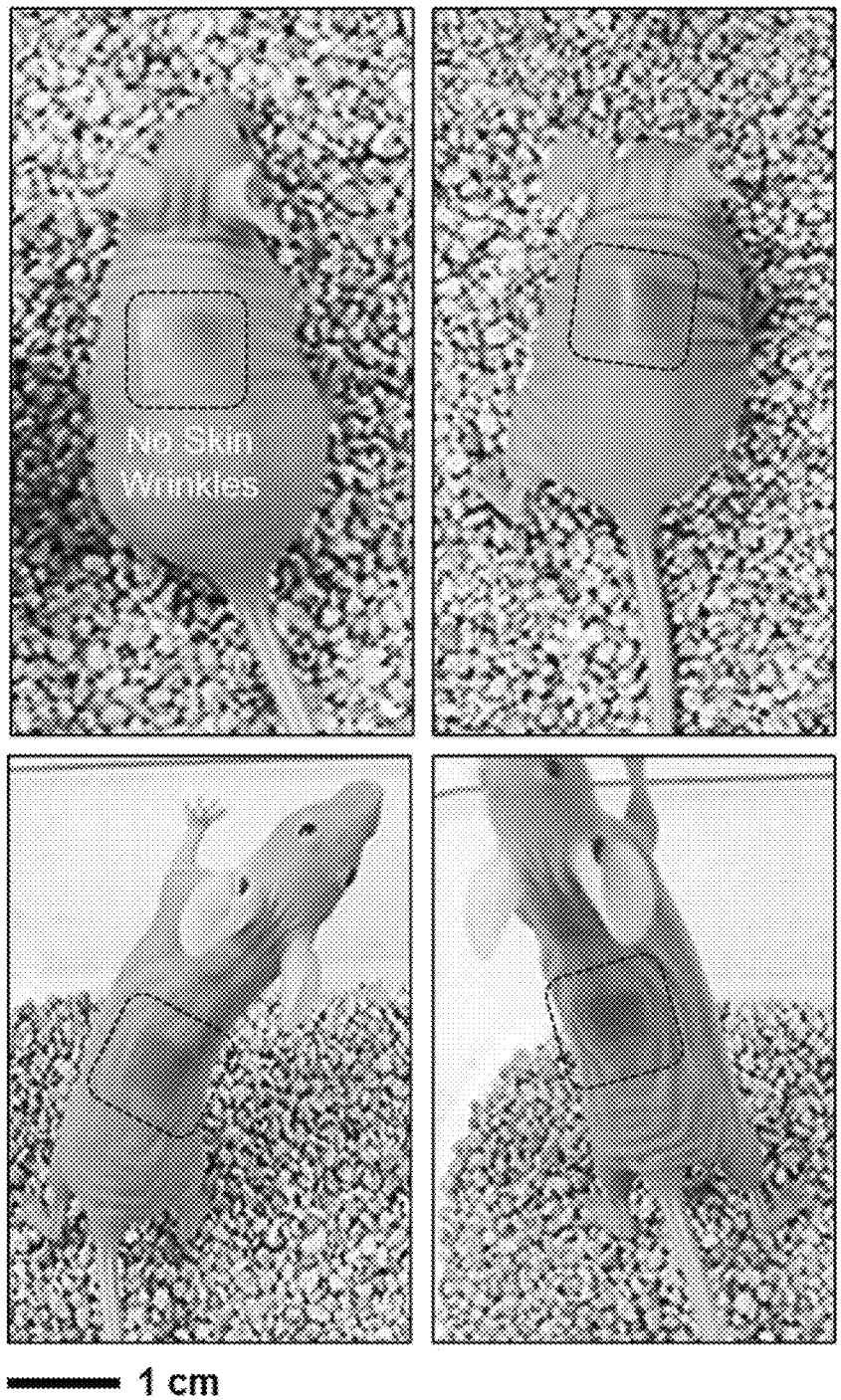
FIG. 19 includes optical images of a nude mouse wearing on its backside a drug delivery device comprising control p-Si needles on a PDMS film.

FIG. 4A shows representative optical images, pointing out the injection sites where p-Si needles were embedded after the PVA film was completely dissolved with saline solution. The size of the p-Si needles was much smaller than that of conventionally-used polymeric microneedles (typically, d>5 μm, D>300 μm, and L>600 μm) and remained nearly unnoticeable on the tissue surface by visual observations (FIG. 18). This aspect may help reduce the risk of irritation or discomfort during/after the injection of the p-Si needles. The mice exhibited normal behaviors without showing any evidence of discomfort against natural movements for the entire period of observation (about three months). FIG. 4B shows corresponding IVIS images, indicating that the fluorescent dyes were uniformly localized over the irregular surface of the epidermis, subcutaneous muscle, and cornea of the mice, and maintained until the florescent dyes were completely absorbed into the body. FIG. 19 shows optical images of a control unit array (1×1 cm$^2$) of p-Si needles integrated with a flexible, yet non-water-soluble PDMS film (200 μm-thick), which was attached on the back of a nude mouse. Of note, no wrinkles were observed on the skin over the PDMS film while other areas of the skin were easily wrinkled according to body movements. These observations imply that the skin underneath the PDMS film experienced occasional interruptions or discomforts due to the physical constraints, highlighting the rationale of eliminating the PDMS film after complete delivery of the p-Si needles.

Tumor relapse after surgical resection that occurs by an outgrowth of residual microtumors remains a significant challenge in current treatments. Systemic chemotherapy and radiotherapy are often employed to prevent the recurrence of residual tumors, but these methods lead to toxic side effects and do not provide a long-lasting protection unless frequently repeated. Sustained topical delivery of therapeutic drug cargos with precisely controlled doses for a prolonged time, after surgical resection, may reduce the risk of tumor relapse with minimal side effects and improved convenience of patients and healthcare providers.

Figure 5A:
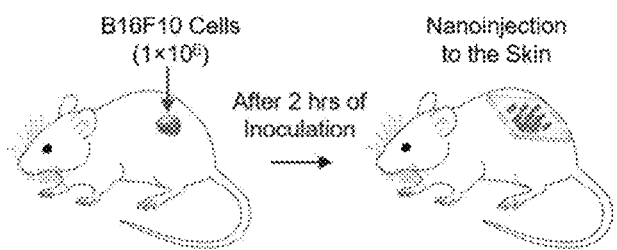
FIGS. 5A through 5F represent evaluations in a murine melanoma model in vivo.
Figure 5B:
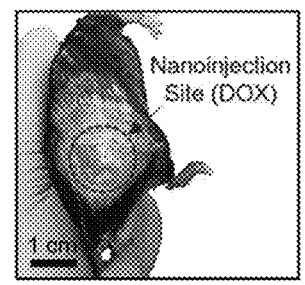
Figure 5C:
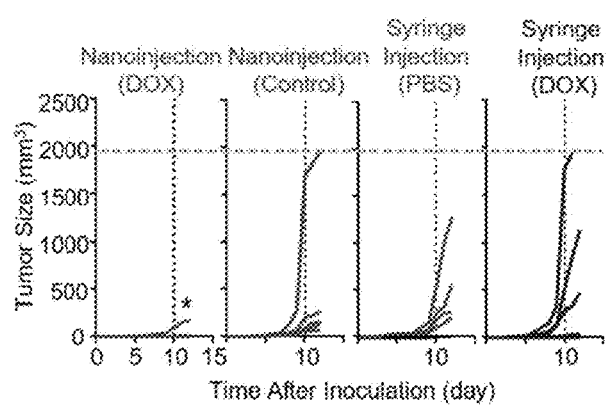
Figure 5D:
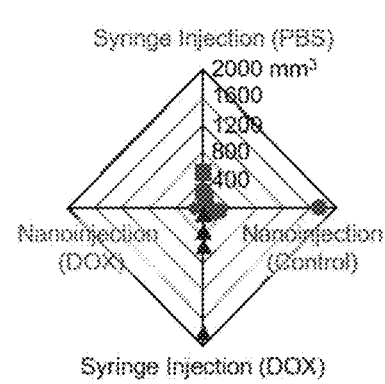
Figure 5E:
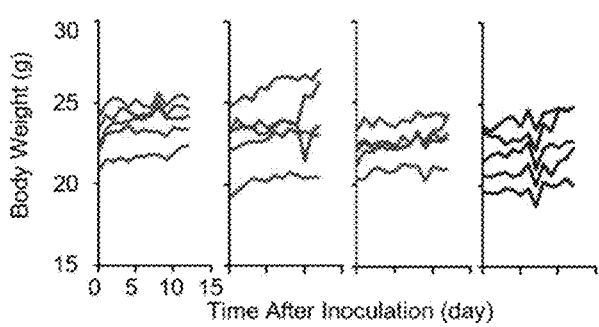
Figure 5F:
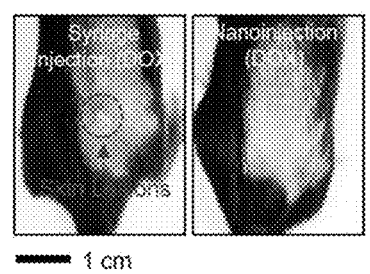
Figure 20:
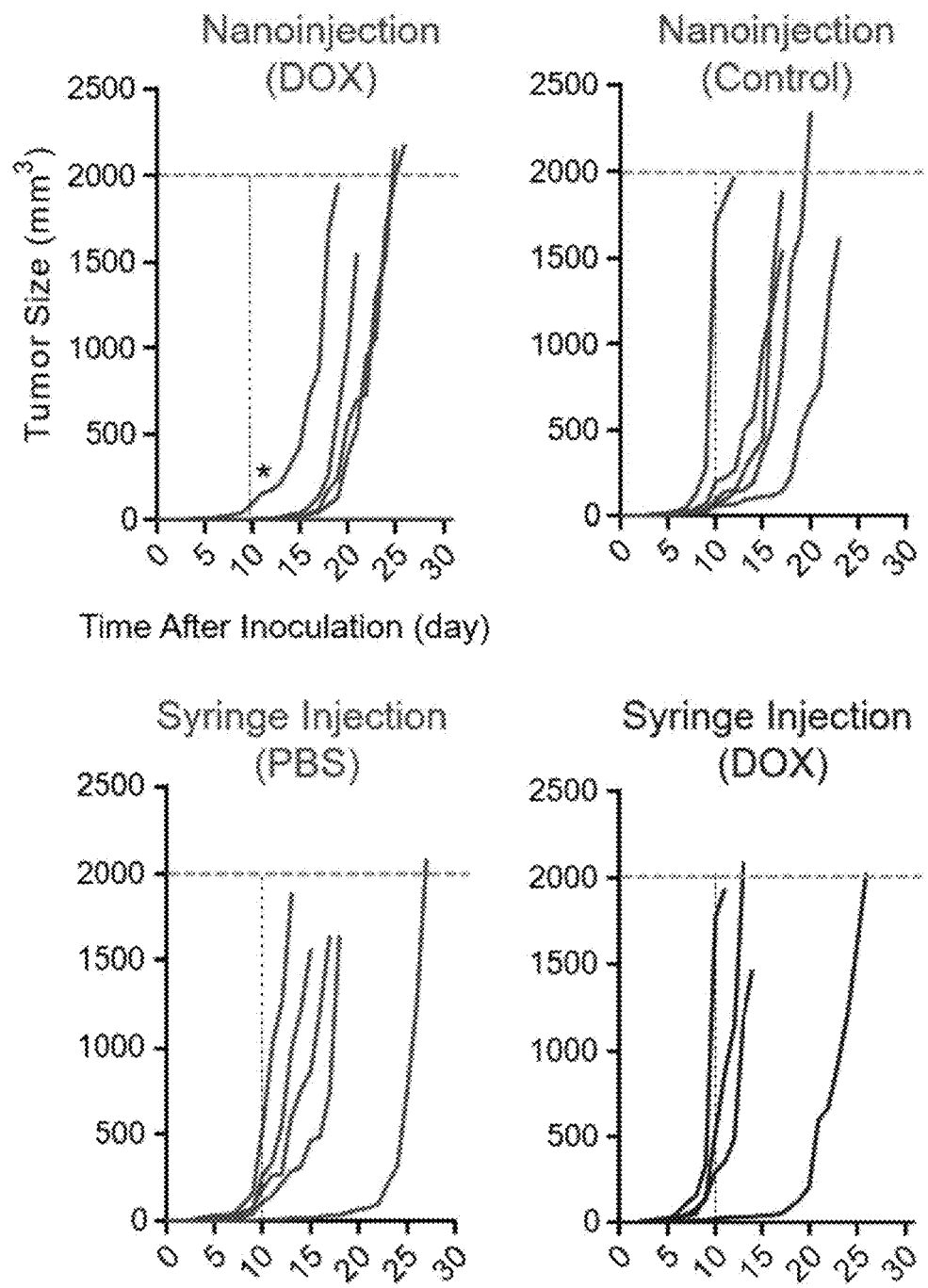
FIG. 20 includes measurement results of tumor size (n=5 per group). Mice were humanely sacrificed when tumor sizes reached an endpoint of 2000 mm$^3$. *$p<0.05$, compared to the control syringe injection (DOX) using ANOVA.
Figure 21:
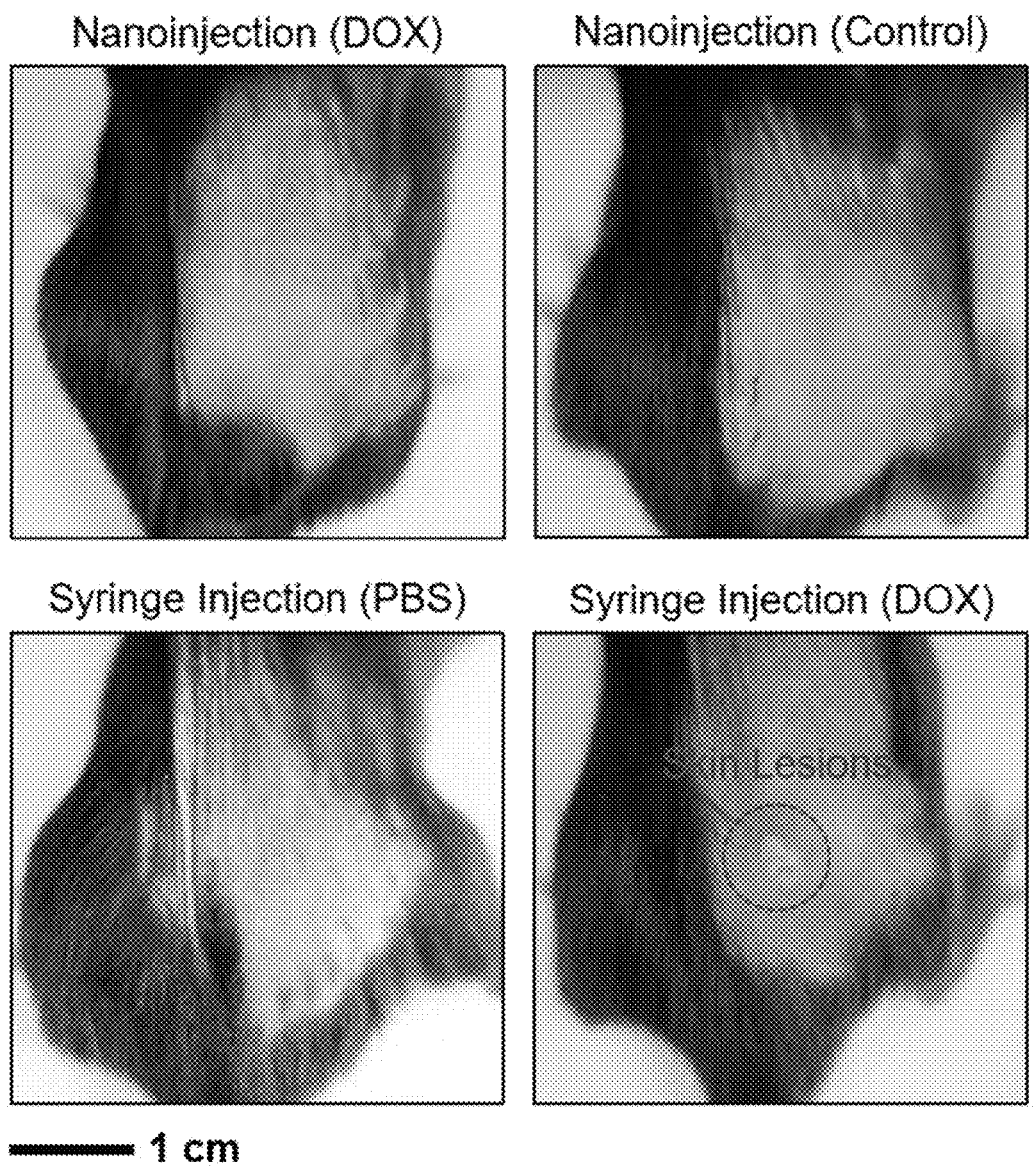
FIG. 21 includes enlarged optical images of the treated sites of mice at ten days post-injection.

The utility of the p-Si needles in the inhibition of post-surgical residual melanoma was tested using C57BL/6 mice and syngeneic B16F10 melanoma cells. The mice were subcutaneously inoculated with 1×10$^6$ B16F10 melanoma cells to mimic a situation where melanoma resection is incomplete and residual cells are present. Following two hours of the subcutaneous inoculation, an array of p-Si needles (1×1 cm$^2$, d=150 nm, D=1 μm, and L=50 μm) covalently-linked (amide) with 50 μl of DOX (about 20 μg) or without DOX (control) were applied to the tumor inoculation site (FIG. 5A). This basic procedure for injection of the p-Si needles will be hereinafter referred to as "nanoinjection". A representative photograph in FIG. 5B highlights the nanoinjection site on the shaved skin of a mouse. The mouse receiving the p-Si needles moved freely without any sign of discomfort. Two other control groups of mice were intratumorally administered using a medical 28 G insulin syringe with a single dose of PBS (50 μl) and DOX (50 μl), representing no-treatment control and a conventional bolus injection, respectively. FIG. 5C shows that, in the mice treated with the nanoinjection of DOX, tumor growth was suppressed over ten days post-inoculation. In contrast, significant growth of the tumors occurred in four out of five mice treated with the control nanoinjection (without DOX), all five mice with the syringe injection of PBS, and four out of five mice with the syringe injection of DOX during the same period, followed by rapid increase to reach the endpoint tumor size of 2000 mm$^3$ (FIG. 20). FIG. 5D shows comparisons of sizes of the tumors at ten days post-inoculation. All of these treatments were well tolerated by the mice with negligible weight loss during the surviving period (FIG. 5E); however, local skin lesions were observed on the mice treated with the syringe injection of DOX (FIG. 5F and FIG. 21), which is a typical side effect of the drug. The superior anti-tumor efficacy of the nanoinjected DOX compared to the bolus-injected DOX with the same dose was attributable to the prolonged maintenance of effective local concentration based on the sustained drug release (FIGS. 3F through 3H). These findings support that the sustained release of DOX at the skin with residual melanoma cells by nanoinjection can provide a prolonged suppression of tumor growth without adverse effects as compared to a bolus injection.

While the invention has been described in terms of specific embodiments, it is apparent that other forms could be adopted by one skilled in the art. For example, the physical configuration of the delivery device and its components could differ from that shown, and materials and processes/methods other than those noted could be used. Therefore, the scope of the invention is to be limited only by the following claims.

The invention claimed is:

1. A drug delivery device comprising:
   a flexible film;
   an array of nanoscopic, porous needles attached to a surface of the flexible film; and
   a therapeutic drug cargo loaded onto individual needles of the array of nanoscopic, porous needles;
   wherein the flexible film is formed of a material that dissolves when contacted with a water-based solution comprising a saline solution.

2. The drug delivery device of claim 1, wherein the individual needles are configured to gradually degrade over time when in contact with living tissue causing release of the therapeutic drug cargo.

3. The drug delivery device of claim 2, wherein the individual needles degrade via gradual hydrolysis due to fluids in the living tissue.

4. The drug delivery device of claim 1, wherein the therapeutic drug cargo is covalently bonded to surfaces of the individual needles.

5. The drug delivery device of claim 1, wherein the individual needles are configured to degrade and release the therapeutic drug cargo in a manner that reaches a sustained predetermined dose at or above a minimum inhibitory concentration of the therapeutic drug cargo.

6. The drug delivery device of claim 5, wherein the predetermined dose is above a half maximal inhibitory concentration ($IC_{50}$) value.

7. The drug delivery device of claim 1, wherein the water-based solution comprises an interstitial fluid.

8. The drug delivery device of claim 1, wherein the flexible film is configured to dissolve in one minute or less.

9. The drug delivery device of claim 1, wherein the individual needles have minimum tip diameters of 50 to 900 nm, base diameters of 0.9 to 5 μm, and lengths of 1 to 100 μm.

10. The drug delivery device of claim 1, wherein the individual needles have an average porosity of about 0 to 80 percent.

11. A method of fabricating a drug delivery device comprising a flexible film, an array of nanoscopic, porous needles attached to a surface of the flexible film, and a therapeutic drug cargo loaded onto individual needles of the array of nanoscopic, porous needles, the method comprising:
   forming an array of vertically-ordered, nanoscopic, porous pillars on a substrate, individual pillars of the array of vertically-ordered nanoscopic porous pillars having distal ends extending away from the substrate and proximal ends adjacent the substrate, the individual pillars each having an undercut formed therein at the proximal end thereof that has a minimum diameter of the individual pillar;
   forming the flexible film parallel to the substrate with an air gap therebetween, wherein distal ends of the individual pillars are embedded in the flexible film;
   peeling the flexible film away from the substrate such that proximal ends of the individual pillars break away from the substrate at the undercuts thereof and the distal ends of the individual pillars remain embedded in the flexible film, the individual pillars remaining in the flexible film defining the array of nanoscopic, porous needles; and
   loading the individual needles with the therapeutic drug cargo.

12. The method of claim 11, wherein the flexible film is formed by:
   spin-casting the substrate having the individual pillars thereon with a pre-cured solution while allowing the air gap to form therebetween due to surface tension; and
   thermally annealing the spin-cast, pre-cured solution to form the flexible film.

13. A method comprising:
   providing a drug delivery device that includes an array of nanoscopic, porous needles attached to a surface of a flexible film;
   applying the drug delivery device to living tissue such that the surface of the flexible film contacts the living tissue and individual needles of the array of nanoscopic, porous needles are inserted into the tissue; and
   dissolving the flexible film while leaving the individual needles inserted in the tissue by applying a water-based saline solution to the flexible film, wherein the water-based solution comprises a saline solution;
   wherein the individual needles degrade in the living tissue over time causing release of a therapeutic drug cargo that was loaded onto the individual needles.

14. The method of claim 13, wherein the individual needles degrade via gradual hydrolysis due to fluids in the living tissue.

15. The method of claim 13, wherein the water-based solution comprises an interstitial fluid.

16. The method of claim 13, wherein the therapeutic drug cargo is covalently bonded to surfaces of the individual needles.

* * * * *